US012729185B2

(12) United States Patent
Chang et al.

(10) Patent No.: US 12,729,185 B2
(45) Date of Patent: Sep. 8, 2026

(54) PREPARATION METHOD FOR PYRIMIDINE-2-AMINE

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Sukbok Chang, Daejeon (KR); Won Seok Ham, Daejeon (KR); Jianbo Zhang, Daejeon (KR); Hoonchul Choi, Daejeon (KR)

(73) Assignees: INSTITUTE FOR BASIC SCIENCE, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 345 days.

(21) Appl. No.: 18/692,655

(22) PCT Filed: Sep. 19, 2022

(86) PCT No.: PCT/KR2022/013972

§ 371 (c)(1),
(2) Date: Mar. 15, 2024

(87) PCT Pub. No.: WO2023/043292

PCT Pub. Date: Mar. 23, 2023

(65) Prior Publication Data

US 2024/0383863 A1 Nov. 21, 2024

(30) Foreign Application Priority Data

Sep. 17, 2021 (KR) ........................ 10-2021-0124953
Sep. 15, 2022 (KR) ........................ 10-2022-0116511

(51) Int. Cl.

| | |
|---|---|
| ***C07D 239/42*** | (2006.01) |
| ***B01J 23/42*** | (2006.01) |
| ***B01J 31/22*** | (2006.01) |
| ***C07D 239/48*** | (2006.01) |
| ***C07D 401/04*** | (2006.01) |
| ***C07D 403/04*** | (2006.01) |
| ***C07D 405/04*** | (2006.01) |
| ***C07D 417/04*** | (2006.01) |
| ***C07D 487/04*** | (2006.01) |
| ***C07F 7/18*** | (2006.01) |

(52) U.S. Cl.

CPC ............ *C07D 239/42* (2013.01); *B01J 23/42* (2013.01); *B01J 31/2208* (2013.01); *C07D 239/48* (2013.01); *C07D 401/04* (2013.01); *C07D 403/04* (2013.01); *C07D 405/04* (2013.01); *C07D 417/04* (2013.01); *C07D 487/04* (2013.01); *C07F 7/1892* (2013.01); *B01J 2231/44* (2013.01); *B01J 2531/74* (2013.01)

(58) Field of Classification Search

CPC .. C07D 239/42; C07D 239/48; C07D 401/04; C07D 403/04; C07D 405/04; C07D 417/04; C07D 487/04; C07D 215/42; C07D 241/20; B01J 23/42; B01J 31/2208; B01J 2231/44; B01J 2531/74; B01J 2231/76; B01J 31/122; C07F 7/1892; C07F 9/17; C07B 43/04

See application file for complete search history.

(56) References Cited

U.S. PATENT DOCUMENTS

| | | | |
|---|---|---|---|
| 2004/0220201 | A1 | 11/2004 | Bilodeau et al. |
| 2013/0303532 | A1 | 11/2013 | Koppitz et al. |

FOREIGN PATENT DOCUMENTS

| | | | |
|---|---|---|---|
| KR | 10-2004-0041178 A | 5/2004 | |
| KR | 10-1767602 B1 | 8/2017 | |
| KR | 10-2018-0134966 A | 12/2018 | |
| KR | 10-2019-0043842 A | 4/2019 | |
| WO | 03/037895 A1 | 5/2003 | |
| WO | 2009/016460 A2 | 2/2009 | |

OTHER PUBLICATIONS

Kumaresan et al. Synthesis, characterization and anti-inflammatory activy of some novel pyrimidin-2-amines on carrageenan-induced paw edema in balb/c mice (Journal of Chemical and Pharmaceutical Research, 2014, 6(10): 593-606). (Year: 2014).*

Korean Notice of Allowance dated Apr. 8, 2024 in Application No. 10-2022-0116511.

Ming-Ming Wang et al., "Diamine Synthesis via the Nitrogen-Directed Azidation of o-and It-C-C Bonds", Supporting Information, pp. S1-S142 no date.

Caroline Hadad et al., "4-Arylvinyl-2,6-di(pyridin-2-yl)pyrimidines: Synthesis and Optical Properties", Supporting Information, pp. S1-S30 no date.

T. Mathur et al., "Synthesis, Characterization and Antimicrobial Screening of New Bi- Heterocyclic Azo Derivative of Quinazoline Compound", Heterocyclic Letters, Aug-Oct. 2019, pp. 447-453, vol. 9, No. 4.

Tara R. Rheault et al., "The Discovery of Dabrafenib: a Selective Inhibitor of Raf Kinases With Anti-Tumor Activity Against B-Raf Driven Tumors", Supporting Information, pp. 1-8 no date.

Minoru Yamaji et al., "Blue fluorescence from BF2 complexes of N, O-benzamide ligands: Synthesis structure and photophysical properties", The Supporting Information pp. 1-17.

Gongming Yang et al., "Direct access to pyrimidines through organocatalytic inverse-electron-demand Diels-Alder reaction of ketones with 1,3,5-triazine", RSC Advances, 2015, pp. 76759-76763, 5.

(Continued)

*Primary Examiner* — Kamal A Saeed
*Assistant Examiner* — Meghan C Heasley
(74) *Attorney, Agent, or Firm* — Sughrue Mion, PLLC

(57) ABSTRACT

The present invention relates to a preparation method for pyrimidine-2-amine and, more specifically, to a method for preparing a pyrimidine-2-amine compound via a pyrimidine-2-iminium salt intermediate by using a nucleophilic imine-type reagent, in which various amino functional groups are selectively introduced at position No. 2 of pyrimidine.

19 Claims, No Drawings

(56) References Cited

OTHER PUBLICATIONS

Xiaodong Xiong et al., "Highly ortho-Selective Chlorination of Anilines Using a Secondary Ammonium Salt Organocatalyst", Angewandte Chime International Edition, 2016, pp. 1-6, 55.
Michael Hoffelner et al., "New 2-aminopyrimidine derivatives and their antitrypanosomal and antiplasmodial activities", Monatshefte fur Chemie-Chemical Monthly, 2020, pp. 1375-1385, vol. 151, No. 9.
Prithwish Ghosh et al., "Site-Selective C-H Alkylation of Diazine-N-Oxides Enabled by Phosphonium Ylides", Supporting Information, pp. S1-S116 no date.
Deng, Lanqing et al., "A New Synthesis of 2-Amino-4,5-substituted Pyrimidine Derivatives", Chinese Journal of Organic Chemistry, 2012, pp. 1141-1145, vol. 32, No. 6.
International Search Report for PCT/KR2022/013972, dated Dec. 30, 2022.

* cited by examiner

PREPARATION METHOD FOR PYRIMIDINE-2-AMINE

CROSS REFERENCE TO RELATED APPLICATIONS

This application is a National Stage of International Application No. PCT/KR2022/013972 filed Sep. 19, 2022, claiming priority based on Korean Patent Application No. 10-2021-0124953 filed Sep. 17, 2021 and Korean Patent Application No. 10-2022-0116511 filed Sep. 15, 2022, the entire disclosures of which are incorporated herein by reference.

TECHNICAL FIELD

The present invention relates to a method of preparing a pyrimidin-2-amine compound, and more particularly, to a method of preparing a pyrimidin-2-amine compound in which various amino functional groups are selectively introduced to position 2 of pyrimidine via a pyrimidin-2-iminium salt intermediate using a nucleophilic imine-type reagent.

BACKGROUND ART

N-heteroaryl amine is an important molecular skeleton which is present in a large number in a molecule showing various physiological activities or medicinal effects. In particular, 2-aminopyridine is a core structural motif which is widely spread in bioactive molecules. However, it is difficult to introduce an amine functional group to carbon number 2 of pyrimidine through direct functionalization.

Since 29 out of 100 best-selling low molecular medicines in 2020 are N-heteroaryl amine, selective and efficient preparation of aminated N-heteroarene may promote discovery of biologically active molecules. Frequently used approaches for the synthesis of N-heteroaryl amine includes nucleophilic aromatic substitution and transition-metal-mediated cross-coupling. Since direct carbon-hydrogen (C—H) functionalization has an inherent problem in selectivity control due to ubiquity of a C—H bond in an organic molecule, it is not required for a pre-functionalized substrate, and thus, may be an attractive alternative. A regioselective heteroarene C—H amination reaction allows rapid approach to a synthetic intermediate. Strategies such as C—H metalation, N-radical substitution, nucleophilic functionalization and others were implemented for synthesizing aminated N-heteroarene of various arrays.

However, in spite of research efforts on direct N-heteroarene amination, the range of a C—H bond which is approachable in the N-heteroaromatic substrate is still largely limited.

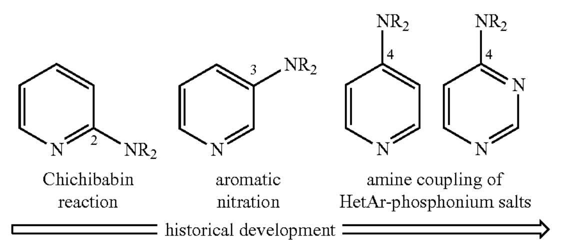

-continued

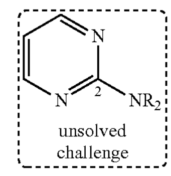

11 out of 100 top-selling small molecule drugs

Actually, a Chichibabin reaction and aromatic nitration are representative approaches to C2- and C3-selective amination of pyridine, respectively, and modern application of the Chichibabin reaction led to development of a mild method for C2-H amination of pyridine and quinoline. Recently, C4-selective amination of pyridine and pyrimidine was proved by McNally and his co-workers through mediation of a heteroaryl phosphonium salt.

However, 2-aminopyridine is an important skeleton found in numerous commercially available medicines and pesticides, and is a very preferable structural motif in discovery chemistry, but a general strategy for C2-selective amination of pyrimidine has not been found to date.

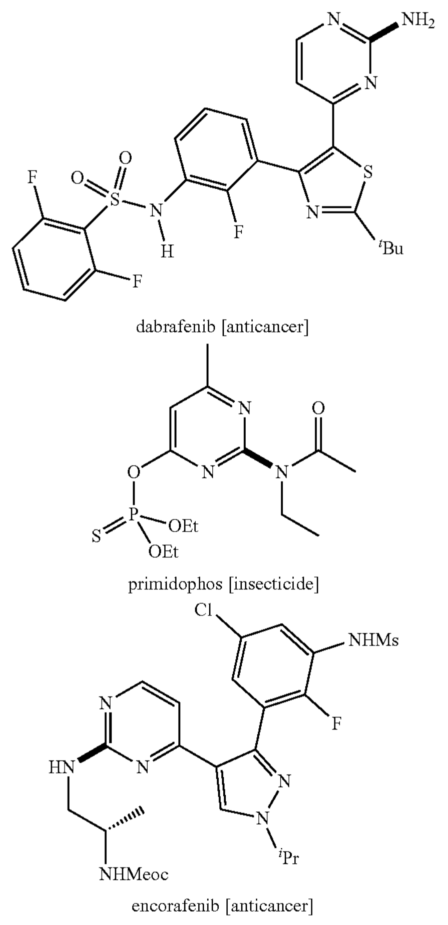

dabrafenib [anticancer]

primidophos [insecticide]

encorafenib [anticancer]

Therefore, development of a method of efficiently preparing pyrimidin-2-amine by C2-selective amination of pyrimidine acting as a structural core motif which is important in medicines, pesticides, and various chemical fields is desperately needed.

DISCLOSURE

Technical Problem

The present inventors studied hard and made an effort in order to selectively aminate C2 of pyrimidine, and as a result, confirmed that a pyridinyl-2-iminium salt acting as a branch point which may be subsequently converted into all types of pyrimidin-2-amine (1°, 2°, and 3° amine forms) through a combination of activated pyrimidine and nucleophilic imine-type reagent (electron-deficient pyridine compound or imidoyl chloride compound) is synthesized, and it is amine derivatized to synthesize a pyrimidin-2-amine compound.

An object of the present invention is to provide a C2-selective nucleophilic functionalized platform which provides a synthesis handle for branching/divergent synthesis of 2-aminopyridine by converting pyrimidine into a pyrimidin-2-iminium salt.

Another object of the present invention is to provide a method of preparing a pyrimidin-2-amine compound which may be useful as a core structure in various fields such as medicines and pesticides.

Technical Solution

The present disclosure provides a method of preparing a pyrimidin-2-amine compound in which various amino functional groups are selectively introduced to position 2 of pyrimidine via a pyrimidin-2-iminium salt intermediate, using a nucleophilic imine-type reagent.

In one general aspect, a method of preparing a pyrimidin-2-amine compound includes: 1) oxidizing a pyrimidine compound of the following Chemical Formula 2 to prepare a pyrimidine-N-oxide intermediate; 2) following step 1), in-situ activating the pyrimidine-N-oxide intermediate in the presence of a trifluoromethanesulfonic anhydride ($Tf_2O$) and reacting with a pyridine reagent of the following Chemical Formula 3-1 to prepare a pyrimidine-2-pyridinium salt; and 3) following step 2), aminolyzing the pyrimidine-2-pyridinium salt to prepare a pyrimidin-2-amine compound of the following Chemical Formula 1-1, wherein steps 1) and 2) are performed as in-situ continuous processes without a separation process:

[Chemical Formula 1-1]

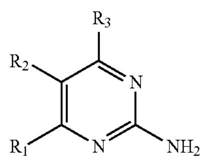

[Chemical Formula 2]

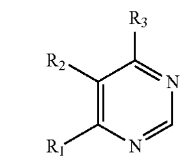

[Chemical Formula 3-1]

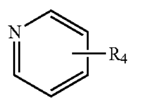

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

$R_4$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, —$OSiR_{a1}R_{a2}R_{a3}$, -$L_1$-$NR_{b1}$-$L_2$-$R_{b2}$, and —$CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is -$L_3$-$R_{d1}$, $L_3$ is C1-C20 alkylene, and $R_{d1}$ is cyano, halogen, or nitro.

In another general aspect, a method of preparing a cyclic (2-enamino)pyrimidine compound includes: 1) oxidizing a pyrimidine compound of the following Chemical Formula 2 to prepare a pyrimidine-N-oxide intermediate; 2) following step 1), in-situ activating the pyrimidine-N-oxide intermediate in the presence of a trifluoromethanesulfonic anhydride ($Tf_2O$) and reacting with a pyridine reagent of the following Chemical Formula 3-2 to prepare a pyrimidine-2-pyridinium salt; and 3) following step 2), partially reducing the pyrimidine-2-pyridinium salt to prepare a cyclic (2-enamino)pyrimidine compound of the following Chemical Formula 1-2, wherein steps 1) and 2) are performed as in-situ continuous processes without a separation process:

[Chemical Formula 1-2]

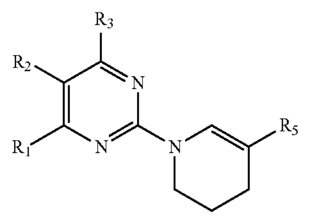

[Chemical Formula 2]

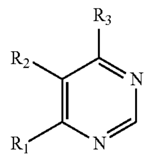

[Chemical Formula 3-2]

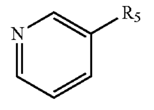

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

$R_5$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, —$OSiR_{a1}R_{a2}R_{a3}$, -$L_1$-$NR_{b1}$-$L_2$-$R_{b2}$, and —$CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is -$L_3$-$R_{d1}$, $L_3$ is C1-C20 alkylene, and $R_{d1}$ is cyano, halogen, or nitro.

In still another general aspect, a method of preparing a pyrimidin-2-substituted amine compound includes: 1) oxidizing a pyrimidine compound of the following Chemical Formula 2 to prepare a pyrimidine-N-oxide intermediate; 2) following step 1), reacting the pyrimidine-N-oxide intermediate with an imidoyl chloride compound of the following Chemical Formula 4-1 in the presence of a trifluoromethanesulfonic anhydride ($Tf_2O$) to prepare a pyrimidin-2-iminium salt; and 3) following step 2), treating the pyrimidin-2-iminium salt with sodium bicarbonate, or reducing or hydrolyzing the pyrimidin-2-iminium salt to prepare a pyrimidin-2-substituted amine compound of the following Chemical Formula 1-3, wherein steps 1) and 2) are performed as in-situ continuous processes without a separation process:

[Chemical Formula 1-3]

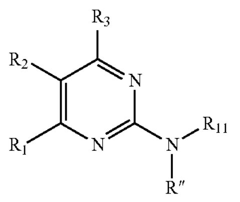

[Chemical Formula 2]

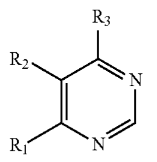

[Chemical Formula 4-1]

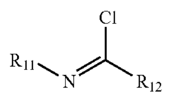

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

R" is hydrogen, —C(═O) $R_{12}$, or —$CH_2R_{12}$;

$R_{11}$ is C1-C20 alkyl, C6-C20 aryl, allyl, halo C1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl;

$R_{12}$ is C1-C20 alkyl or C6-C20 aryl;

$R_4$ is halo C1-C20 alkyl, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, —$OSiR_{a1}R_{a2}R_{a3}$, -$L_1$-$NR_{b1}$-$L_2$-$R_{b2}$, and —$CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is -$L_3$-$R_{d1}$, $L_3$ is C1-C20 alkylene, and $R_{d1}$ is cyano, halogen, or nitro.

Advantageous Effects

According to the preparation method of the present invention, a pyrimidin-2-amine compound in which various amine functional groups, ranging from primary to tertiary amines, are selectively introduced to position 2 of the pyrimidine may be efficiently prepared via a pyrimidine-2-iminium salt intermediate which is produced by reacting an electron deficient pyridine compound or an imidoyl chloride compound as a nucleophilic imine-type reagent with activated pyrimidine.

According to the preparation method of the present invention, a C2-selective nucleophilic functionalized platform which provides a synthesis handle for branching/divergent synthesis of 2-aminopyridine by converting pyrimidine into a pyrimidin-2-iminium salt may be provided.

In addition, according to the preparation method of the present invention, the electron deficient pyridine compound used in the reaction may be recovered and recycled, and a pyrimidin-2-amine compound may be mass produced from pyrimidine, which thus has high commercial availability.

In addition, the pyrimidin-2-amine compound prepared according to the preparation method of the present invention may be applied very usefully as an intermediate and a synthesis unit in various fields such as various natural products and medicines.

BEST MODE

Hereinafter, the present invention will be described in detail. Technical terms and scientific terms used in the present specification have the general meaning understood by those skilled in the art to which the present invention pertains unless otherwise defined, and a description for the known function and configuration obscuring the present invention will be omitted in the following description.

It should be understood that in the present specification, unless otherwise required in the context, the terms “comprises” and “comprising” include a suggested step or constituent element, or a group of steps or constituent elements, but imply that any other step or constituent element or any group of steps or constituent groups is not excluded.

In the present specification, “substituent”, “radical”, “group”, “moiety”, and “fragment” may be used interchangeably.

In the present specification, “$C_A$-$C_B$” refers to “the number of carbons being A or more and B or less”.

In the present specification, "substitution" means that a hydrogen atom bonded to a carbon atom of a compound is changed into another substituent, and a substituted position is not limited as long as it is a position at which a hydrogen atom is substituted, that is, a position at which a substituent may be substituted, and when two or more are substituted, two or more substituents may be the same as or different from each other.

The term "alkyl" in the present specification refers to a monovalent straight chain or branched chain saturated hydrocarbon radical composed of only carbon and hydrogen atoms. The alkyl may have 1 to 20 carbon atoms. The alkyl may have 1 to 10 carbon atoms. The alkyl may have 1 to 7 carbon atoms. An example of the alkyl radical includes methyl, ethyl, propyl, isopropyl, butyl, isobutyl, t-butyl, pentyl, hexyl, octyl, nonyl, decyl, dodecyl, tetradecyl, and the like, but is not limited thereto.

The term "alkoxy" in the present specification refers to an —O-alkyl radical, wherein "alkyl" is as defined above.

A specific example thereof includes methoxy, ethoxy, isopropoxy, butoxy, isobutoxy, t-butoxy, and the like, but is not limited thereto.

The term "aryl" in the present specification refers to a monovalent organic radical of an aromatic ring derived from aromatic hydrocarbon by removal of one hydrogen, including a single- or fused ring system containing appropriately 4 to 7, preferably 5 or 6 ring atoms in each ring, and even a form in which a plurality of aryls are connected by a single bond. As the ring atom, it may have 6 to 20 carbon atoms, preferably 6 to 12 carbon atoms. A specific example thereof includes phenyl, naphthyl, biphenyl, anthryl, indenyl, fluorenyl, and the like, but is not limited thereto.

The term "heteroaryl" in the present specification refers to a monovalent radical of a heteroaromatic ring which is an aryl group containing 1 to 4 heteroatoms selected from N, O, and S as an aromatic ring skeletal atom, and carbons as remaining aromatic ring skeletal atoms, and is a 5- or 6-membered monocyclic heteroaryl and a polycyclic heteroaryl fused with one or more benzene rings, which may be partially saturated. In addition, the heteroaryl in the present invention also includes a form in which one or more heteroaryls are linked by a single bond. An example of the heteroaryl group includes pyrrolyl, pyrazolyl, quinolyl, isoqinolyl, pyridyl, pyrimidinyl, oxazolyl, thiazolyl, thiadiazolyl, triazolyl, imidazolyl, benzoimidazolyl, isooxazolyl, benzoisooxazolyl, thiophenyl, benzothiophenyl, furyl, benzofuryl, and the like, but is not limited thereto.

The term "halo" or "halogen" in the present specification refers to a halogen group element, and includes, for example, fluoro, chloro, bromo, and iodo.

The term "haloalkyl" in the present specification refers to an alkyl radical substituted with at least one halogen, in which "alkyl" is as defined above. An example of the haloalkyl radical includes fluoromethyl, trifluoromethyl, bromomethyl, perfluoroethyl, and the like, but is not limited thereto.

The term "cycloalkyl" in the present specification is a nonaromatic carbocyclic monovalent radical composed of one or more rings, and may include all of saturated or unsaturated monocycle, polycycle, or spirocycle forms. A specific example thereof may include cyclopropyl, cyclobutyl, cyclopentyl, cyclohexyl, norbornyl, bicyclo[1.1.1]pentyl, bicyclo[3.1.0]hexyl, bicyclo[4.1.0]heptyl, bicyclo[2.2.1]heptyl, adamantly, decalinyl, and the like, but is not limited thereto.

The term "alkenyl" in the present specification is a straight chain or branched chain unsaturated hydrocarbon monovalent radical containing one or more double bonds between two or more carbon atoms, and may be partially saturated. A specific example thereof includes ethenyl, 1-propenyl, 2-propenyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, isoprenyl, geranyl, 5-tetradecenyl, and the like, but is not limited thereto.

The term "alkylene" in the present specification refers to a divalent straight chain or branched chain saturated hydrocarbon divalent group composed of only carbon and hydrogen atoms, and specifically, includes methylene, ethylene, propylene, isopropylene, butylene, isobutylene, t-butylene, pentylene, hexylene, octylene, nonylene, and the like, but is not limited thereto.

The term "arylene" in the present specification refers to a divalent organic radical of an aromatic ring derived from aromatic hydrocarbon, including a single- or fused ring system containing appropriately 4 to 7, preferably 5 or 6 ring atoms in each ring, and even a form in which a plurality of aryls are linked by a single bond. As an example, it includes naphthylene, biphenylene, terphenylene, anthrylene, indenylene, fluorenylene, pyrene, phenanthrylene, triphenylenylene, pyrenylene, perylenylene, chrysenylene, naphthacenylene, fluororantenylene, and the like, or a combination thereof, but is not limited thereto.

The present invention relates to a method of preparing a pyrimidin-2-amine compound, and more particularly, to a method of efficiently preparing a pyrimidin-2-amine compound in which various amine functional groups ranging from primary to tertiary amines are selectively introduced to position 2 of pyrimidine via a pyrimidin-2-iminium salt intermediate produced by reacting with activated pyrimidine using an electron deficient pyridine compound or imidoyl chloride compound as a nucleophilic imine-type reagent.

According to an exemplary embodiment of the present invention, a method of preparing a pyrimidin-2-amine compound including: 1) oxidizing a pyrimidine compound of the following Chemical Formula 2 to prepare a pyrimidine-N-oxide intermediate; 2) following step 1), in-situ activating the pyrimidine-N-oxide intermediate in the presence of a trifluoromethanesulfonic anhydride ($Tf_2O$) and reacting with a pyridine reagent of the following Chemical Formula 3-1 to prepare a pyrimidine-2-pyridinium salt; and 3) following step 2), aminolyzing the pyrimidine-2-pyridinium salt to prepare a pyrimidin-2-amine compound of the following Chemical Formula 1-1, wherein steps 1) and 2) are performed as in-situ continuous processes without a separation process, is provided.

[Chemical Formula 1-1]

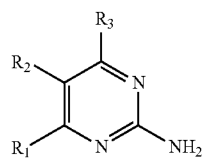

[Chemical Formula 2]

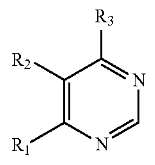

-continued

[Chemical Formula 3-1]

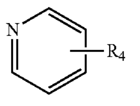

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

$R_4$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, —$SiR_{a1}R_{a2}R_{a3}$, -$L_1$-$NR_{b1}$-$L_2$-$R_{b2}$, and —$CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is -$L_3$-$R_{d1}$, $L_3$ is C1-C20 alkylene, and $R_{d1}$ is cyano, halogen, or nitro.

The method of preparing a pyrimidin-2-amine compound of Chemical Formula 1-1 according to the present invention may efficiently produce a pyrimidin-2-amine compound in which an amine functional group is selectively introduced to position 2 of pyrimidine through oxidation and activation of a pyrimidine compound of Chemical Formula 2 as a starting material, a subsequent reaction with an electron deficient pyridine compound as a nucleophilic imine-type reagent, and an aminolysis process. According to the present invention, a wide range of substrates with various substituents introduced as a starting material may be employed.

The oxidation in step 1) may be performed under an oxidizing agent, a rhenium catalyst, or a combination thereof, and preferably, may be catalytic oxidation performed in the presence of an oxidizing agent and a rhenium catalyst. That is, when the oxidation reaction is performed with the oxidizing agent in the presence of the rhenium catalyst which is an oxidation catalyst, a pyrimidine-N-oxide intermediate may be produced with high purity and high yield only by a simple separation process.

The rhenium catalyst may be one or a mixture of two or more selected from methyltrioxorhenium (MTO), ethyltrioxorhenium (ETO), rhenium(VII) oxide ($Re_2O_7$), rhenium (V) oxide ($Re_2O_5$), rhenium(IV) oxide ($ReO_2$), and ammonium perrhenate (APR), and preferably, may use methyltrioxorhenium (MTO).

An amount of the rhenium catalyst used is not particularly limited, but may be in a range of 1.0 to 30.0 mol %, 2.0 to 25.0 mol %, or 5.0 to 20.0 mol % with respect to the pyrimidine compound of Chemical Formula 2.

The oxidizing agent may be hydrogen peroxide or a hydrogen peroxide adduct, and the hydrogen peroxide adduct may be urea-hydrogen peroxide or sodium percarbonate, preferably hydrogen peroxide, and more specifically a 50% hydrogen peroxide aqueous solution.

An amount of the oxidizing agent used is not particularly limited, but may be in a range of 1 to 5 equivalents, 1.5 to 5 equivalents, or 2 to 5 equivalents with respect to the pyrimidine compound of Chemical Formula 2.

Specifically, the oxidation in step 1) may be catalytic oxidation performed in the presence of methyltrioxorhenium (MTO) and hydrogen peroxide, more specifically in the presence of methyltrioxorhenium and a 50% hydrogen peroxide aqueous solution.

During the catalytic oxidation of step 1), trifluoromethanesulfonic acid may be further added, and may be added in a range of 1 equivalent or more, specifically 1 to 3 equivalents or 1 to 2 equivalents with respect to the pyrimidine compound of Chemical Formula 2.

The amount of the trifluoromethanesulfonic anhydride ($Tf_2O$) used in step 2) is not particularly limited, but may be in a range of 1 equivalent or more, specifically 1 to 3 equivalents or 1 to 2 equivalents with respect to the pyrimidine compound of Chemical Formula 2.

The pyridine reagent of Chemical Formula 3-1 in step 2) may be used in an excessive amount, specifically in a range of 1.5 to 5 equivalents or 2 to 3 equivalents with respect to the pyrimidine compound of Chemical Formula 2.

The pyrimidine-2-pyridinium salt intermediate prepared through 1) and 2) steps may act as a C2-selective nucleophilic functionalized platform which provides a synthesis handle for branching/divergent synthesis of 2-aminopyrimidine.

The aminolysis in step 3) may be performed in the presence of ammonia water. During amine derivatization of the pyrimidine-2-pyridinium salt, ammonia is used as an amino source, thereby obtaining a primary amine product (Chemical Formula 1-1).

In an exemplary embodiment, reactions in all steps may be performed under mild conditions, and any reaction temperature is allowed as long as it is a common temperature used in organic synthesis, but specifically, step 1) may be performed at 20 to 30° C., step 2) may be performed at 0 to 30° C., and step 3) may be performed at 60 to 90° C., and the temperature may be appropriately adjusted, if necessary. A reaction time varies depending on reaction materials, amounts of the reaction materials, the type of solvents, and the amount of solvents, and is not particularly limited.

In an exemplary embodiment, the reactions in all steps may be performed under an organic solvent, and the organic solvent does not need to be limited as long as it does not react with the reaction materials. As an example, the organic solvent may be dichloromethane (DCM), dichloroethane, tetrachloroethane, acetonitrile (MeCN), nitromethane, toluene, benzene, ethanol (EtOH), and the like, alone or in combination of two or more. Specifically, one or more selected from dichloromethane, acetonitrile, and ethanol may be used as a reaction solvent.

A preparation process of the pyrimidin-2-amine compound of Chemical Formula 1-1 through steps 1) to 3) is shown in the following Reaction Formula 1. As shown in Reaction Formula 1, the pyrimidine compound of Chemical Formula 2 is catalytically oxidized to form a pyrimidine-N-oxide intermediate, which is in-situ activated in the presence of a trifluoromethanesulfonic anhydride and also reacted with the pyridine reagent of Chemical Formula 3-1 to form a pyrimidine-2-pyridinium salt of Chemical Formula A-1 as a key intermediate, which may be directly aminolyzed without separation and purification to prepare the pyrimidin-2-amine compound of Chemical Formula 1-1:

[Reaction Formula 1]

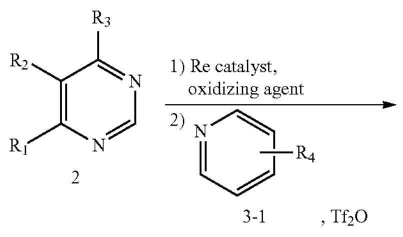

-continued

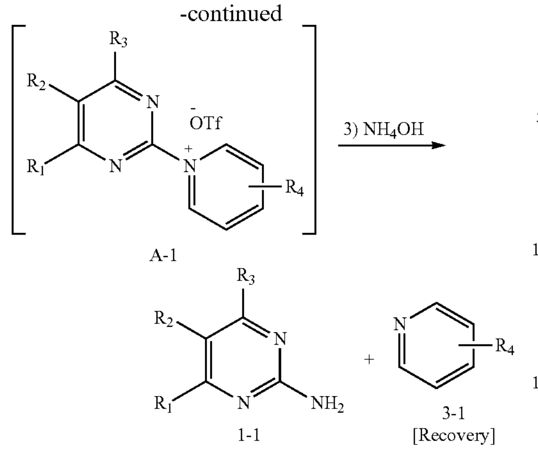

A-1

1-1

3-1 [Recovery]

wherein $R_1$ to $R_4$ are as defined above.

In an exemplary embodiment, in Chemical Formulae 1-1 and 2, $R_1$, $R_2$, and $R_3$ may be C1-C10 alkyl, hydroxy C1-C10 alkyl, $—(CH_2)_a—OSiR_{a1}R_{a2}R_{a3}$, C3-C10 cycloalkyl, C6-C12 aryl, halo C6-C12 aryl, C1-C10 alkoxy, —CH═CH—Ar, C3-C10 heteroaryl, or $—NHC(═O)Ar_1$, and $R_2$ and $R_3$ may be linked by

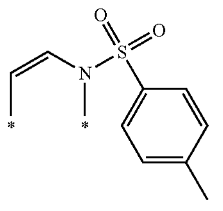

to form a ring; a may be an integer of 1 to 10; $R_{a1}$, $R_{a2}$, and $R_{a3}$ may be independently of one another C1-C10 alkyl; Ar may be C6-C12 aryl or halo C6-C12 aryl; $Ar_1$ may be C6-C12 aryl; the heteroaryl of $R_1$ to $R_3$ may be further substituted by any one or more selected from C1-C10 alkyl, $-L_1-NH-L_2-R_{b2}$, and $—CHR_{c1}R_{c2}$; $L_1$ may be C6-C12 arylene or halo C6-C12arylene, $L_2$ may be $SO_2$ or C═O; $R_{b2}$ may be C1-C10 alkoxy, C6-C12 aryl, or halo C6-C12 aryl; $R_{c1}$ may be C3-C10 cycloalkyl; and $R_{c2}$ may be $—(CH_2)_b—CN$, and b may be an integer of 1 to 10; and in Chemical Formula 3-1, $R_4$ may be haloC1-C10 alkyl or C6-C20arylcarbonyl.

According to another exemplary embodiment of the present invention, a method of preparing a cyclic (2-enamino) pyrimidine compound including: 1) oxidizing a pyrimidine compound of the following Chemical Formula 2 to prepare a pyrimidine-N-oxide intermediate; 2) following step 1), in-situ activating the pyrimidine-N-oxide intermediate in the presence of a trifluoromethanesulfonic anhydride and reacting with a pyridine reagent of the following Chemical Formula 3-2 to prepare a pyrimidine-2-pyridinium salt; and 3) following step 2), partially reducing the pyrimidine-2-pyridinium salt to prepare a cyclic (2-enamino)pyrimidine compound of the following Chemical Formula 1-2, wherein steps 1) and 2) are performed as in-situ continuous processes without a separation process, is provided:

[Chemical Formula 1-2]

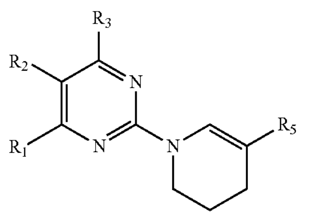

-continued

[Chemical Formula 2]

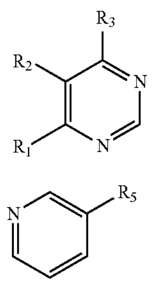

[Chemical Formula 3-2]

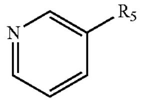

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or $—NR'C(═O)Ar_1$, or $R_1$ to $R_3$ may be linked to an adjacent substituent to form a ring;

$R_5$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, $—SiR_{a1}R_{a2}R_{a3}$, $-L_1-NR_{b1}-L_2-R_{b2}$, and $—CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is $-L_3-R_{d1}$, $L_3$ is C1-C20 alkylene, and $R_{d1}$ is cyano, halogen, or nitro.

The method of preparing the cyclic (2-enamino)pyrimidine compound of Chemical Formula 1-2 may efficiently produce the cyclic (2-enamino)pyrimidine compound in which a partially reduced cyclic amine functional group is selectively introduced to position 2 of pyrimidine through oxidation and activation of the pyrimidine compound of Chemical Formula 2 as a starting material, a subsequent reaction with an electron deficient pyridine compound which is a nucleophilic imine-type reagent, and a partial reduction process. According to the present invention, a wide range of substrates with various substituents introduced as a starting material may be employed.

Though steps 1) and 2) are as described above, the pyridine reagent of Chemical Formula 3-2 in step 2) may be used in an excessive amount, specifically in a range of 1.5 to 5 equivalents or 2 to 3 equivalents with respect to the pyrimidine compound of Chemical Formula 2.

The pyrimidine-2-pyridinium salt intermediate prepared through 1) and 2) steps may act as a C2-selective nucleophilic functionalized platform which provides a synthesis handle for branching/divergent synthesis of 2-aminopyrimidine.

The partial reduction in step 3) may be performed in the presence of hydrogen gas, and a platinum group metal catalyst including platinum, palladium, rhodium, and/or ruthenium, and specifically, may be performed in the presence of hydrogen gas and $PtO_2$. The metal catalyst, specifically $PtO_2$ may be used in a range of 1.0 to 20.0 mol %, 1 to 15 mol %, or 3 to 10 mol % with respect to the pyrimidine compound of Chemical Formula 2.

In an exemplary embodiment, reactions in all steps may be performed under mild conditions, and any reaction temperature is allowed as long as it is a common temperature used in organic synthesis, but specifically, the oxidation of step 1) may be performed at 20 to 30° C., step 2) may be performed at 0 to 30° C., and step 3) may be performed at 20 to 30° C., and the temperature may be appropriately adjusted, if necessary. A reaction time varies depending on reaction materials, amounts of the reaction materials, the type of solvents, and the amount of solvents, and is not particularly limited.

In an exemplary embodiment, the reactions in all steps may be performed under an organic solvent, and the organic solvent does not need to be limited as long as it does not react with the reaction materials. As an example, the organic solvent may be dichloromethane (DCM), dichloroethane, tetrachloroethane, acetonitrile (MeCN), nitromethane, toluene, benzene, ethanol (EtOH), and the like, alone or in combination of two or more. Specifically, one or more selected from dichloromethane, acetonitrile, and ethanol may be used as a reaction solvent.

A process of preparing the cyclic (2-enamino)pyrimidine compound of Chemical Formula 1-2 through steps 1) to 3) is shown in the following Reaction Formula 2. As shown in Reaction Formula 2, the pyrimidine compound of Chemical Formula 2 is catalytically oxidized to form a pyrimidine-N-oxide intermediate, which is in-situ activated in the presence of a trifluoromethanesulfonic anhydride and also reacted with the pyridine reagent of Chemical Formula 3-2 to form a pyrimidine-2-pyridinium salt of Chemical Formula A-2 as a key intermediate, which may be directly partially reduced without separation and purification to prepare the cyclic (2-enamino)pyrimidine compound of Chemical Formula 1-2:

[Reaction Formula 2]

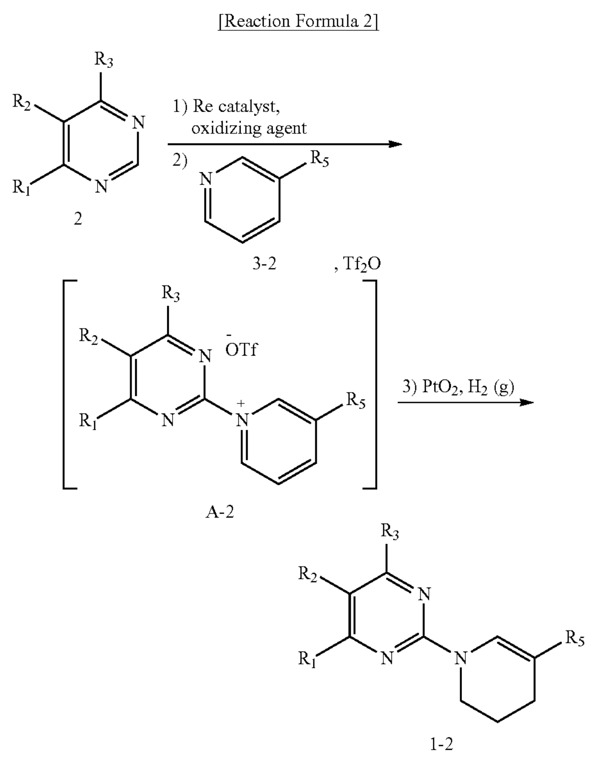

wherein $R_1$ to $R_3$ and $R_5$ are as defined above.

In an exemplary embodiment, in Chemical Formulae 1-2 and 2, $R_1$, $R_2$, and $R_3$ may be independently of one another hydrogen, C1-C10 alkyl, hydroxy C1-C10 alkyl, $—(CH_2)_a—OSiR_{a1}R_{a2}R_{a3}$, C3-C10 cycloalkyl, C6-C12 aryl, halo C6-C12 aryl, C1-C10 alkoxy, —CH═CH—Ar, C3-C10 heteroaryl, or $—NHC(═O)Ar_1$, and the $R_2$ and $R_3$ may be linked by

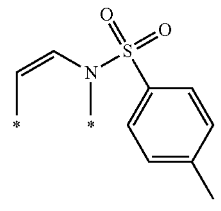

to form a ring; a may be an integer of 1 to 10; $R_{a1}$, $R_{a2}$, and $R_{a3}$ may be independently of one another C1-C10 alkyl; Ar may be C6-C12 aryl or halo C6-C12aryl; $Ar_1$ may be C6-C12 aryl; the heteroaryl of $R_1$ to $R_3$ may be further substituted by any one or more selected from C1-C10alkyl, $-L_1-NH-L_2-R_{b2}$, and $—CHR_{c1}R_{c2}$; $L_1$ may be C6-C12 arylene or halo C6-C12 arylene, $L_2$ may be $SO_2$ or C═O; $R_{b2}$ may be C1-C10 alkoxy, C6-C12 aryl, or halo C6-C12 aryl; $R_{c1}$ may be C3-C10 cycloalkyl; and $R_{c2}$ may be $—(CH_2)_b—CN$, and b may be an integer of 1 to 10; and in Chemical Formula 3-2, $R_5$ may be halo C1-C10 alkyl.

According to another exemplary embodiment of the present invention, a method of preparing a pyrimidin-2-substituted amine compound including: 1) oxidizing a pyrimidine compound of the following Chemical Formula 2 to prepare a pyrimidine-N-oxide intermediate; 2) following step 1), reacting the pyrimidine-N-oxide intermediate with an imidoyl chloride compound of the following Chemical Formula 4-1 in the presence of a trifluoromethanesulfonic anhydride to prepare a pyrimidin-2-iminium salt; and 3) following step 2), treating the pyrimidin-2-iminium salt with sodium bicarbonate, or reducing or hydrolyzing the pyrimidin-2-iminium salt to prepare a pyrimidin-2-substituted amine compound of the following Chemical Formula 1-3, wherein steps 1) and 2) are performed as in-situ continuous processes without a separation process, is provided:

[Chemical Formula 1-3]

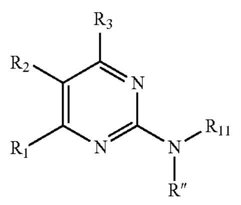

[Chemical Formula 2]

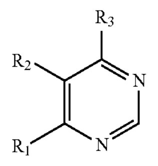

[Chemical Formula 4-1]

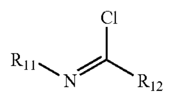

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or $—NR'C(═O)Ar_1$, or $R_1$ to $R_3$ may be linked to an adjacent substituent to form a ring;

R" is hydrogen, $—C(═O)\ R_{12}$, or $—CH_2R_{12}$;

$R_{11}$ is C1-C20 alkyl, C6-C20 aryl, allyl, halo C1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl;

$R_{12}$ is C1-C20 alkyl or C6-C20 aryl;

$R_4$ is halo C1-C20 alkyl, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, $—OSiR_{a1}R_{a2}R_{a3}$, $-L_1-NR_{b1}-L_2-R_{b2}$, and $—CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is $-L_3-R_{d1}$, $L_3$ is C1-C20 alkylene, and $R_{d1}$ is cyano, halogen, or nitro.

The method of preparing the pyrimidin-2-substituted amine compound of Chemical Formula 1-3 according to the present invention may efficiently produce a pyrimidin-2-substituted amine compound in which a substituted amine functional group is selectively introduced to position 2 of pyrimidine through oxidation and activation of the pyrimidine compound of Chemical Formula 2 as a starting material, subsequent activation and reaction with an imidoyl chloride compound which is a nucleophilic imine-type reagent, and a post-treatment process. According to the present invention, a wide range of substrates with various substituents introduced as a starting material may be employed.

Step 1) is as described above.

The imidoyl chloride compound of Chemical Formula 4-1 used in step 2) may be prepared by reacting the amide compound of Chemical Formula 4 with oxalyl chloride in the presence of an organic base, and it may be prepared immediately before use and reacted in the presence of the pyrimidine-N-oxide intermediate formed in step 1) and the trifluoromethanesulfonic anhydride without separation and purification.

[Chemical Formula 4]

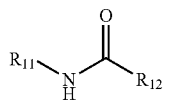

wherein $R_{11}$ and $R_{12}$ are as defined above.

The imidoyl chloride compound of Chemical Formula 4-1 is prepared by reacting 1 to 5 equivalents or 2 to 3 equivalents of the amide compound of Chemical Formula 4, 1 to 5 equivalents or 2 to 3 equivalents of oxalyl chloride, and 1 to 5 equivalents or 2 to 3 equivalents of an organic base with respect to the pyrimidine compound of Chemical Formula 2, and may be directly used in the next reaction in-situ without a separate separation and purification process. The used organic base may be selected from pyridine, triethylamine, diisopropylamine, N,N-diisopropylethylamine, 2,6-lutidine, or a mixture thereof, specifically, may be 2,6-lutidine.

In step 2), an amount of the trifluoromethanesulfonic anhydride ($Tf_2O$) used is not particularly limited, but may be in a range of 1 equivalent or more, specifically 1 to 3 equivalents or 1 to 2 equivalents with respect to the pyrimidine compound of Chemical Formula 2.

In step 2), the imidoyl chloride reagent of Chemical Formula 4-1 may be used in an excessive amount, specifically in a range of 1.5 to 5 equivalents or 2 to 3 equivalents with respect to the pyrimidine compound of Chemical Formula 2.

The pyrimidin-2-iminium salt intermediate prepared through 1) and 2) steps may act as a C2-selective nucleophilic functionalized platform which provides a synthesis handle for branching/divergent synthesis of 2-aminopyrimidine.

Step 3) may be a step of preparing a pyrimidin-2-amide compound of the following Chemical Formula 1-3A by a treatment with sodium bicarbonate:

[Chemical Formula 1-3A]

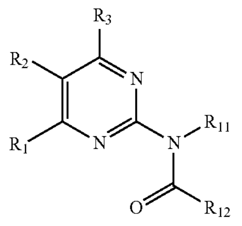

wherein $R_1$ to $R_3$, $R_{11}$, and $R_{12}$ are as defined above.

Step 3) may be a step of hydrogenating the iminium ion by a reaction with a reducing agent to form a tertiary amine type product, and specifically, may be a step of reducing with a reducing agent selected from sodium triaxetoxyborohydride ($Na(CH_3COO)_3BH$), sodium borohydride ($NaBH_4$), sodium cyanoborohydride ($NaBH_3CN$), zinc borohydride ($Zn(BH_4)_2$), lithium aluminum hydride ($LiAlH_4$), and lithium cyanoborohydride ($LiBH_3CN$) to prepare a pyrimidin-2-disubstituted amine compound of the following Chemical Formula 1-3B:

[Chemical Formula 1-3B]

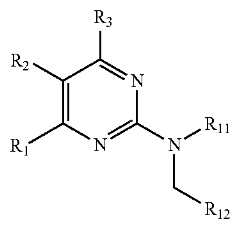

wherein $R_1$ to $R_3$, $R_{11}$, and $R_{12}$ are as defined above.

Step 3) may be a step of forming a secondary amine product through hydrolysis, and specifically, may be a step of preparing a pyrimidin-2-monosubstituted amine compound of the following Chemical Formula 1-3C by a treatment with methanol and sodium hydroxide:

[Chemical Formula 1-3C]

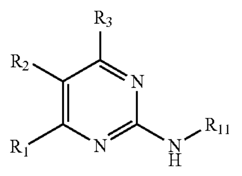

wherein $R_1$ to $R_3$ and $R_{11}$ are as defined above.

In an exemplary embodiment, reactions in all steps may be performed under mild conditions, and any reaction temperature is allowed as long as it is a common temperature used in organic synthesis, but specifically, the oxidation of step 1) may be performed at 20 to 30° C., step 2) may be performed at 0 to 30° C., and step 3) may be performed at 20 to 70° C., and the temperature may be appropriately adjusted, if necessary. A reaction time varies depending on reaction materials, amounts of the reaction materials, the type of solvents, and the amount of solvents, and is not particularly limited.

In an exemplary embodiment, the reactions in all steps may be performed under an organic solvent, and the organic solvent does not need to be limited as long as it does not react with the reaction materials. As an example, the organic solvent may be dichloromethane (DCM), dichloroethane, tetrachloroethane, acetonitrile (MeCN), nitromethane, toluene, benzene, ethanol (EtOH), and the like, alone or in combination of two or more. Specifically, one or more selected from dichloromethane, acetonitrile, and ethanol may be used as a reaction solvent.

A preparation process of the pyrimidine-2-substituted amine compound of Chemical Formula 1-3 through steps 1) to 3) is shown in the following Reaction Formula 3. As shown in Reaction Formula 3, the pyrimidine compound of Chemical Formula 2 is catalytically oxidized to form a pyrimidine-N-oxide intermediate of Chemical Formula A-0, which is in-situ activated in the presence of a trifluoromethanesulfonic anhydride and also reacted with the imidoyl chloride reagent of Chemical Formula 4-1 to form a pyrimidin-2-iminium salt of Chemical Formula A-3 as a key intermediate, which is directly treated with sodium bicarbonate without separation and purification or reduced or hydrolyzed to prepare the pyrimidin-2-substituted amine compound of Chemical Formula 1-3 (R" is hydrogen, —C(═O) $R_{12}$, or —$CH_2R_{12}$):

[Reaction Formula 3]

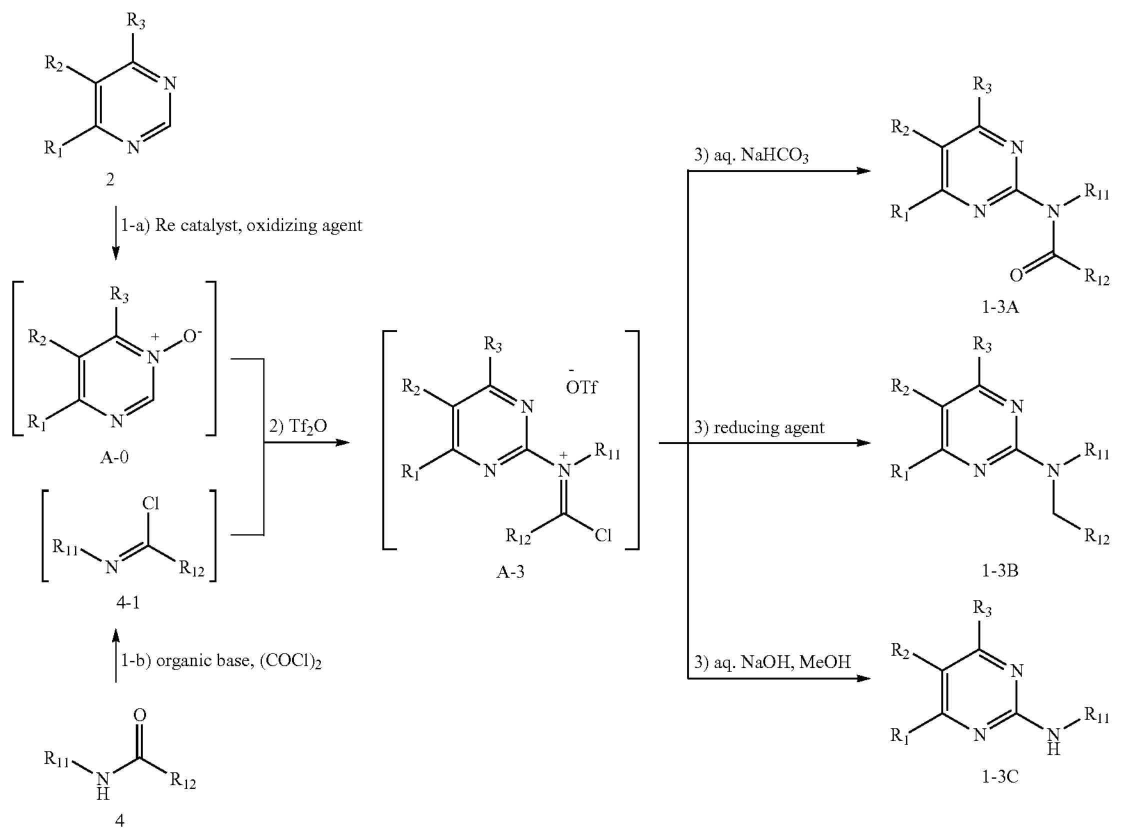

wherein $R_1$ to $R_3$, $R_{11}$, and $R_{12}$ are as defined above.

In an exemplary embodiment, in Chemical Formulae 1-3A, 1-3B, 1-3C, and 2, $R_1$, $R_2$, and $R_3$ may be independently of one another hydrogen, C1-C10 alkyl, hydroxy C1-C10 alkyl, —$(CH_2)_a$—$OSiR_{a1}R_{a2}R_{a3}$, C3-C10 cycloalkyl, C6-C12 aryl, halo C6-C12 aryl, C1-C10 alkoxy, —CH═CH—Ar, C3-C10 heteroaryl, or —NHC(═O)$Ar_1$, or $R_2$ and $R_3$ may be linked by

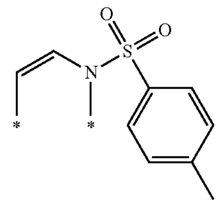

to form a ring; a may be an integer of 1 to 10; $R_{a1}$, $R_{a2}$, and $R_{a3}$ may be independently of one another C1-C10 alkyl; Ar may be C6-C12 aryl or halo C6-C12 aryl; $Ar_1$ may be C6-C12 aryl; the heteroaryl of $R_1$ to $R_3$ may be further substituted by any one or more selected from C1-C10 alkyl, -$L_1$-NH-$L_2$-$R_{b2}$, and —$CHR_{c1}R_{c2}$; $L_1$ may be C6-C12 arylene or halo C6-C12arylene, $L_2$ may be $SO_2$ or C═O; $R_{b2}$ may be C1-C10 alkoxy, C6-C12 aryl, or halo C6-C12 aryl; $R_{c1}$ may be C3-C10 cycloalkyl; and $R_{c2}$ may be —$(CH_2)_b$—CN, and b may be an integer of 1 to 10; and in Chemical Formulae 1-3A, 1-3B, 1-3C, and 4, $R_{11}$ may be C1-C10 alkyl, C6-C12 aryl, allyl, halo C1-C10 alkyl, C6-C12 aryl C1-C10 alkyl, or C3-C10 cycloalkyl, the cycloalkyl may be further substituted by one or more selected from halogen, halo C1-C10 alkyl, and halo C6-C12 aryl; and $R_{12}$ may be C1-C10 alkyl or C6-C12 aryl.

The present invention is a very effective method which may efficiently synthesize pyrimidin-2-amine in one step through C2-selective amination of pyrimidine which acts as an important structural core motif in medicines, pesticides, and various chemical fields. According to the present invention, a pyrimidin-2-amine compound in which various amino functional groups are selectively introduced to position 2 of pyrimidine via a pyrimidin-2-iminium skeleton salt intermediate may be efficiently synthesized, using a nucleophilic imine-type reagent. In addition, since the reaction is performed in-situ and needs only one purification process for separating a final product, the method may have a process advantage.

Hereinafter, the present invention will be described in more detail by the following examples. These examples are only for specifically illustrating the present invention, and it will be apparent to a person with ordinary skill in the art that the scope of the present invention is not limited to these examples according to the gist of the present invention.

All reactions which are not sensitive to air and moisture were performed in the surrounding atmosphere. Concentration was performed by rotary evaporation at 25 to 40° C. at an appropriate pressure. A purified compound was further dried under reduced pressure (0.1 to 1 Torr). A yield shows a purified and spectroscopically pure compound. All operations which are sensitive to air and moisture were performed using oven-dried glass products (130° C. for at least 12 hours) including a standard Schlenk technique under argon atmosphere. Liquids and solutions which are sensitive to air were transferred to a syringe or cannula using a degassed solvent.

[Solvent]

Acetonitrile, dichloromethane, and methanol were purchased from DUKSAN PURE CHEMICALS CO., LTD. and used without further purification. Anhydrous solvents were obtained from Innovative Technology Solvent Drying System. All deuterated solvents were purchased from Eurisotop.

[Chromatography]

Thin layer chromatography (TLC) was performed using a previously coated silica gel 60 F254 plate, and visualized by fluorescence quenching under UV light. A CombiFlash® $R_f$ system equipped with a RediSep® $R_f$ silica column (230 to 400 mesh) using an appropriate eluent system was used to perform flash chromatography.

[Spectroscope and Instruments]

A $^1$H NMR spectrum was obtained using Bruker AV-400 (400 MHz), Bruker AV-500 (500 MHz), or Agilent Technologies DD2 (600 MHz). A $^{13}$C{$^1$H} NMR spectrum was obtained using Bruker AV-500 (125 MHz) or Agilent Technologies DD2 (150 Mhz), and was completely decoupled by broad-band proton decoupling. A $^{19}$F NMR spectrum was obtained using Bruker AS-400 (376 MHz), Bruker AVHD-400 (376 MHz), Bruker AV-500 (470 MHz), or Agilent Technologies DD2 (564 MHz). Chemical shifts were expressed in ppm using solvent resonance as an internal standard. $^1$H NMR: $CDCl_3$, δ 7.26; $CD_3CN$, δ 1.94; $CD_2Cl_2$, δ 5.32; $(CD_3)_2CO$, δ 2.05. $^{13}$C NMR: $CDCl_3$, δ 77.16; $CD_3CN$, δ 1.32; $CD_2Cl_2$, δ 53.84; $(CD_3)_2CO$, δ 29.84. Infrared (IR) spectra were obtained using a Bruker Alpha FT-IR Spectrometer. High resolution mass spectra (HRMS) were obtained using an electrospray ionization (ESI) method in KAIST Analysis Center for Research Advancement (Daejeon) and a fast-atom bombardment (FAB) or electron ionization (EI) method in Korea Basic Science Institute (Daegu). A melting point (m.p.) was measured using Buchi Melting Point M-565. X-ray diffraction (XRD) data was obtained in Bruker D8 QUEST APEX3 coated with paraton-N oil under $N_2$ (g) flows at 173 K.

[Starting Material]

Unless otherwise specified, all commercially available substrates were used without further purification. 2,2,2-Trifluoroethan-1-amine, 3,3-difluorocyclobutan-1-amine hydrochloride, 3-(trifluoromethyl)pyridine, 4-cyanopyridine, 3-benzoylpyridine, N-benzylacetamide, and methyltrioxorhenium(VII) were purchased from TCI Chemical Company, (4-Chlorophenyl)boronic acid, pyrimidine N-oxide, N-methylbenzamide, N-methylacetamide, and acetanilide were purchased from Sigma-Aldrich, 1-(Benzofuran-2-yl)ethan-1-one was purchased from Alfa Aesar, and 1-(4-Fluorophenyl)cyclopropan-1-amine and 5-bromo-4-ethylpyrimidine were purchased from Combi-Blocks. Varenicline tartrate and N-cyclopropyl-2-phenylacetamide were purchased from BLDPharm, Ruxolitinib was purchased from Habo Hong Kong, and N-allylacetamide was purchased from Oakwood Chemical. N-Cyclopropyl-2-phenylacetamide, 2-(pyrimidin-4-yl)ethan-1-ol, methyl 3-[(2,6-difluorophenyl)sulfonamide]-2-fluorobenzoate, 4-(3-iodo-1-isopropyl-1H-pyrazol-4-yl)pyrimidine, {3-[(tert-butoxycarbonyl)amino]phenyl}boronic acid pinacol ester, 4-cyclohexylpyrimidine, N-(pyrimidin-4-yl)benzamide, (E)-4-(4-chlorostyryl)pyrimidine, 4-(pyridin-3-yl)pyrimidine, and N-Cbz-varenicline were synthesized according to [*J. Am. Chem. Soc.* 2021, 143, 11969-11975; WO 2003037895 A1; *ACS Med. Chem. Lett.* 2013, 4, 358-362; WO 2009016460 A2; *Angew. Chem., Int. Ed.* 2016, 55, 16101-16105; *Heterocycles* 2005, 65, 2593-2603; *Inorg. Chem.* 2017, 56, 12514-12519; *J. Org. Chem.* 2012, 77, 4087-4096; *RSC Adv.* 2015, 5, 76759-76763; *Org. Lett.* 2019, 21, 6488-6493] and used.

PREPARATION EXAMPLES: PREPARATION OF STARTING MATERIAL

[Preparation Example 1] Preparation of N-(2,2,2-trifluoroethyl)acetamide (S1)

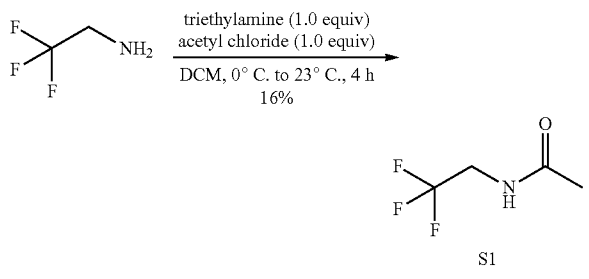

S1

A stirrer bar, 2,2,2-trifluoroethan-1-amine (1.00 mL, 1.26 g, 12.7 mmol, 1.0 equiv.), and anhydrous dichloromethane (25 mL) were charged into an oven-dried 100 mL round bottom flask under argon atmosphere. The stirred solution was cooled to 0° C., and then triethylamine (1.86 mL, 1.35 g, 13.4 mmol, 1.0 equiv.) was added through a syringe. Acetyl chloride (952 μL, 1.05 g, 13.4 mmol, 1.0 equiv.) was added dropwise through a syringe while stirring at 0° C. The mixture was warmed to 23° C. over 5 minutes, and then stirred at the same temperature for 4 hours. The reaction mixture was diluted with dichloromethane (25 mL), and then washed with 1 N hydrochloric acid aqueous solution (10 mL×3). An organic layer was dried with sodium sulfate, filtered, and concentrated under vacuum to obtain a target compound (S1) as a white solid (292 mg, yield: 16%).

m.p.: 61-63° C.; $^1$H NMR (500 MHz, $CD_2Cl_2$) δ 6.60 (br s, 1H), 3.96-3.80 (m, 2H), 2.01 (s, 3H); $^{13}C\{^1H\}$ NMR (125 MHz, $CD_2Cl_2$) δ 171.0, 124.8 (q, J=278.5 Hz), 40.8 (q, J=34.5 Hz), 22.9; $^{19}$F NMR (470 MHz, $CD_2Cl_2$) δ −73.1; IR ($cm^{-1}$): 3263, 3082, 2964, 2864, 1653, 1562, 1377, 1257, 1147, 985, 834; HRMS (EI): Calculated for $C_4H_6F_3NO$ $[M]^+$: 141.0401; Found: 141.0403.

[Preparation Example 2] Preparation of N-[1-(4-fluorophenyl)cyclopropyl]acetamide (S2)

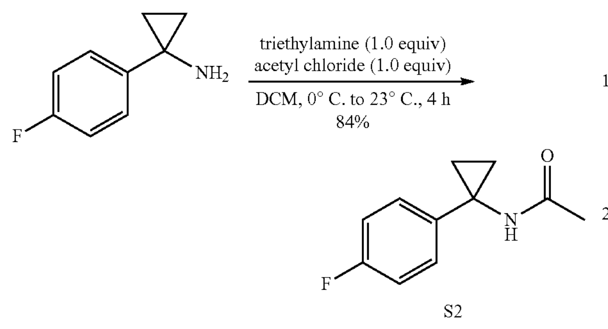

A stirring bar, 1-(4-fluorophenyl)cyclopropan-1-amine (302 mg, 2.00 mmol, 1.0 equiv.), and anhydrous dichloromethane (10 mL) were charged into an oven-dried 50 mL round bottom flask under argon atmosphere. The stirred solution was cooled to 0° C., and then triethylamine (279 μL, 202 mg, 2.00 mmol, 1.0 equiv.) was added through a syringe. Acetyl chloride (142 μL, 157 mg, 2.00 mmol, 1.0 equiv.) was added dropwise through a syringe while stirring at 0° C. The mixture was warmed to 23° C. over 5 minutes, and then stirred at the same temperature for 4 hours. The reaction mixture was diluted with dichloromethane (25 mL) and then washed with a saturated sodium bicarbonate aqueous solution (25 mL), and an organic layer was separated. An aqueous layer was extracted with dichloromethane (25 mL×2). A combined organic layer was dried with sodium sulfate, filtered, and concentrated under vacuum. A residue was purified with silica gel chromatography while eluting with a solvent mixture of n-hexane/ethyl acetate (100/0 to 0/100 (v/v)), thereby obtaining a target compound (S2) as a beige solid (325 mg, yield: 84%).

m.p.: 127-129° C.; $^1$H NMR (500 MHz, $CD_2Cl_2$) δ 7.25-7.18/7.18-7.13 (m, 2H, rotameric), 7.06-7.00/7.00-6.93 (m, 2H, rotameric), 6.34/6.25 (br s, 1H, rotameric), 1.92/1.91 (s, 3H, rotameric), 1.35-1.31/1.24-1.15 (m, 4H, rotameric); $^{13}C\{^1H\}$ NMR (125 MHz, $CD_2Cl_2$) δ 175.1/170.5 (rotameric), 161.8(4)/161.7(9) (d, J=244.4 Hz, rotameric), 139.2/139.1 (d, J=3.0 Hz, rotameric), 127.8/126.4 (d, J=8.0 Hz, rotameric), 115.7/115.2 (d, J=21.4 Hz, rotameric), 36.4/34.8 (rotameric), 23.5/21.7 (rotameric), 20.4/17.9 (rotameric); $^{19}$F NMR (470 MHz, $CD_2Cl_2$) δ −117.8(0)/−117.8(1) (rotameric); IR ($cm^{-1}$): 3287, 3095, 3068, 2934, 1658, 1506, 1365, 1329, 1294, 1213, 1157, 1104, 1035, 1012, 824; HRMS (EI): Calculated for $C_{11}H_{12}FNO$ $[M]^+$: 193.0903; Found: 193.0905.

[Preparation Example 3] Preparation of N-(3,3-difluorocyclobutyl)acetamide (S3)

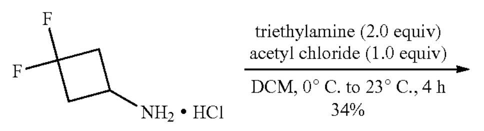

-continued

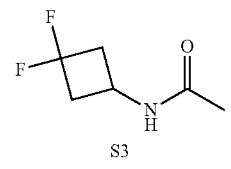

A stirring bar, 3,3-difluorocyclobutan-1-amine hydrochloride (287 mg, 2.00 mmol, 1.0 equiv.), and anhydrous dichloromethane (10 mL) were charged into an oven-dried 50 mL round bottom flask under argon atmosphere. The stirred solution was cooled to 0° C., and then triethylamine (557 μL, 404 mg, 4.00 mmol, 2.0 equiv.) was added through a syringe. Acetyl chloride (142 μL, 157 g, 2.00 mmol, 1.0 equiv.) was added dropwise through a syringe while stirring at 0° C. The mixture was warmed to 23° C. over 5 minutes, and then stirred at the same temperature for 4 hours. The reaction mixture was diluted with dichloromethane (25 mL), and then washed with 1 N hydrochloric acid aqueous solution (10 mL×3). An organic layer was dried with sodium sulfate, filtered, and concentrated under vacuum to obtain a target compound (S3) as a white solid (100 mg, yield: 34%).

m.p.: 97-99° C.; $^1$H NMR (500 MHz, $CD_2Cl_2$) δ 6.34 (br s, 1H), 4.29-4.11 (m, 1H), 3.06-2.86 (m, 2H), 2.60-2.39 (m, 2H), 1.93 (s, 3H); $^{13}C\{^1H\}$ NMR (125 MHz, $CD_2Cl_2$) δ 170.4, 119.4 (dd, J=280.8, 271.2 Hz), 43.2 (dd, J=23.7, 21.9 Hz), 35.0 (dd, J=17.1, 7.4 Hz), 23.2; $^{19}$F NMR (470 MHz, $CD_2Cl_2$) δ −85.0 (d, J=197.7 Hz), −97.9 (d, J=197.7 Hz); IR ($cm^{-1}$): 3304, 3083, 2958, 2925, 2849, 1654, 1550, 1439, 1369, 1244, 1159, 1075, 949, 896; HRMS (EI): Calculated for $C_6H_9F_2NO$ $[M]^+$: 149.0652; Found: 149.0653.

[Preparation Example 4] Preparation of 4-{2-[(triisopropylsilyl)oxy]ethyl}pyrimidine (S4)

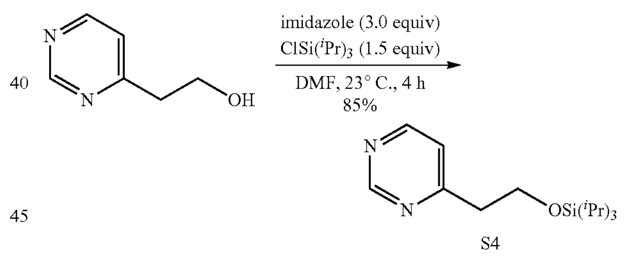

A stirring bar, 2-(pyrimidin-4-yl)ethan-1-ol (123 mg, 0.991 mmol, 1.0 equiv.), and anhydrous N,N-dimethylformamide (4.0 mL) were charged into an oven-dried 25 mL round bottom flask under argon atmosphere. Imidazole (202 mg, 2.97 mmol, 3.0 equiv.) was added to the stirred solution at 23° C. Subsequently, triisopropylsilyl chloride (319 μL, 287 mg, 1.49 mmol, 1.5 equiv.) was added dropwise through a syringe. The mixture was stirred at 23° C. for 4 hours. The reaction mixture was diluted with ethyl acetate (50 mL), and then washed with a saturated lithium chloride aqueous solution (20 mL×3). The organic layer was dried with sodium sulfate, filtered, and concentrated under vacuum. A residue was purified with silica gel chromatography while eluting with a solvent mixture of n-hexane/ethyl acetate (100/0 to 0/100 (v/v)), thereby obtaining a target compound (S4) as a colorless oil (236 mg, yield: 85%).

$^1$H NMR (500 MHz, $CD_2Cl_2$) δ 9.06 (d, J=1.4 Hz, 1H), 8.56 (d, J=5.1 Hz, 1H), 7.27 (dd, J=5.1, 1.4 Hz, 1H), 4.08 (t, J=6.2 Hz, 2H), 2.95 (t, J=6.2 Hz, 2H), 1.09-0.96 (m, 21H); $^{13}C\{^1H\}$ NMR (125 MHz, $CD_2Cl_2$) δ 168.8, 159.0, 156.6, 122.1, 62.5, 41.7, 18.1, 12.3; $^{29}$Si NMR (470 MHz, $CD_2Cl_2$)

δ 13.3; IR ($cm^{-1}$): 2941, 2891, 2865, 1581, 1548, 1463, 1386, 1099, 992, 925, 881, 829; HRMS (FAB): Calculated for $C_{15}H_{29}N_2OSi$ $[M+H]^+$: 281.2044; Found: 281.2046.

[Preparation Example 5] Preparation of 5-(4-chlorophenyl)-4-ethylpyrimidine (S5)

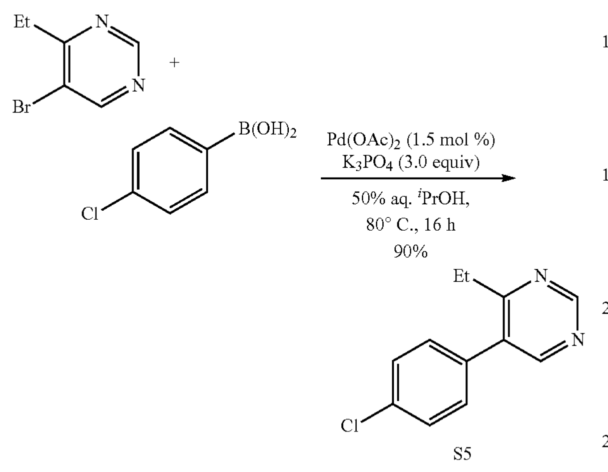

A stirring bar, 5-bromo-4-ethylpyrimidine (935 mg, 5.00 mmol, 1.0 equiv.), (4-chlorophenyl)boronic acid (1173 mg, 7.501 mmol, 1.5 equiv.), palladium(II) acetate (17 mg, 76 μmol, 1.5 mol %), potassium phosphate (3185 mg, 15.00 mmol, 3.0 equiv.), and 50% (v/v) aqueous isopropanol (40 mL) were charged into a 100 mL round bottom flask equipped with a reflux condenser. The mixture was heated to 80° C., and stirred at the same temperature for 16 hours. The reaction mixture was cooled to 23° C., and then diluted with ethyl acetate (50 mL) and brine (50 mL). The organic layer was separated, and an aqueous layer was extracted with ethyl acetate (30 mL×3). A combined organic layer was dried with sodium sulfate, filtered, and concentrated under vacuum. A residue was purified with silica gel chromatography while eluting with a solvent mixture of n-hexane/ethyl acetate (100/0 to 0/100 (v/v)), thereby obtaining a target compound (S5) as a light yellow oil (989 mg, yield: 90%).

$^1H$ NMR (500 MHz, $CD_2Cl_2$) δ 9.06 (s, 1H), 8.46 (s, 1H), 7.49-7.42 (m, 2H), 7.31-7.25 (m, 2H), 2.73 (q, J=7.5 Hz, 2H), 1.19 (t, J=7.5 Hz, 3H); $^{13}C\{^1H\}$ NMR (125 MHz, $CD_2Cl_2$) δ 169.0, 158.0, 156.6, 134.9, 134.6, 133.6, 130.8, 129.2, 28.4, 12.9; IR ($cm^{-1}$): 3032, 2973, 2935, 2875, 1570, 1538, 1490, 1440, 1398, 1091, 999, 827, 741, 686; HRMS (FAB): Calculated for $C_{12}H_{12}ClN_2$ $[M+H]^+$: 219.0684; Found: 219.0689.

[Preparation Example 6] Preparation of 4-(benzofuran-2-yl)pyrimidine (S6)

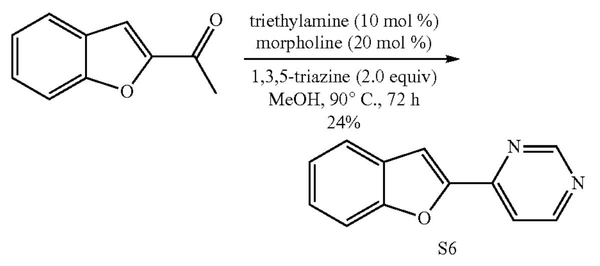

A stirring bar, 1-(benzofuran-2-yl)ethan-1-one (1602 mg, 10.00 mmol, 1.0 equiv.), 1,3,5-triazine (1622 mg, 20.00 mmol, 2.0 equiv.), and methanol (50 mL) were charged into a 100 mL round bottom flask equipped with a reflux condenser. Triethylamine (139 μL, 101 mg, 1.00 mmol, 10 mol %) and morpholine (175 μL, 174 mg, 2.00 mmol, 20 mol %) were continuously added to a stirred mixture through a syringe. The mixture was heated to 90° C., and stirred at the same temperature for 72 hours. The reaction mixture was cooled to 23° C., and then concentrated under vacuum. A residue was purified with silica gel chromatography while eluting with a solvent mixture of n-hexane/ethyl acetate (100/0 to 0/100 (v/v)), thereby obtaining a target compound (S6) as a yellow solid (482 mg, yield: 24%).

m.p.: 109-111° C.; $^1H$ NMR (500 MHz, $CD_2Cl_2$) δ 9.20 (s, 1H), 8.79 (d, J=5.2 Hz, 1H), 7.79 (d, J=5.1 Hz, 1H), 7.70 (d, J=7.6 Hz, 1H), 7.66 (s, 1H), 7.58 (d, J=8.2 Hz, 1H), 7.42 (m, 1H), 7.30 (dd, J=7.5, 7.5 Hz, 1H); $^{13}C\{^1H\}$ NMR (125 MHz, $CD_2Cl_2$) δ 159.4, 158.3, 156.2, 155.7, 153.4, 128.6, 126.9, 124.0, 122.7, 116.2, 112.0, 108.6; IR ($cm^{-1}$): 3031, 3011, 1595, 1568, 1527, 1452, 1384, 1329, 1260, 1051, 986, 925, 883, 819; HRMS (EI) Calculated for $C_{12}H_8N_2O$ $[M]^+$: 196.0637; Found: 196.0632.

[Preparation Example 7] Preparation of N-{3-[2-(tert-butyl)-5-(pyrimidin-4-yl)thiazol-4-yl]-2-fluorophenyl}-2,6-difluorobenzenesulfonamide (S7)

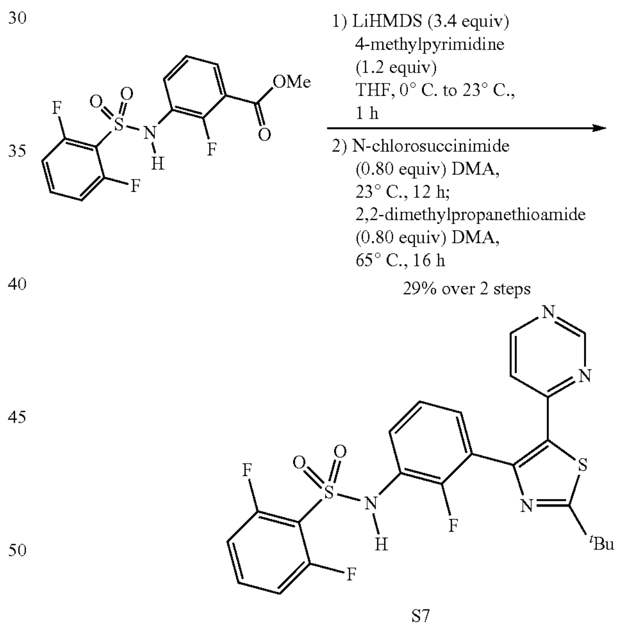

A stirring bar, methyl 3-{(2,6-difluorophenyl)sulfonamido}-2-fluorobenzoate (1.08 g, 3.13 mmol, 1.0 equiv.), and anhydrous THF (10 mL) were charged into an oven-dried 25 mL round bottom flask under argon atmosphere. The mixture was cooled to 0° C., and a THF solution of 1 M LiHMDS (10.5 mL, 10.5 mmol, 3.4 equiv.) was added dropwise through a syringe. The mixture was stirred at 0° C. for 10 minutes, and then a solution of 4-methylpyrimidine (343 μL, 354 mg, 3.76 mmol, 1.2 equiv.) in anhydrous THF (6.0 mL) was added dropwise. The mixture was warmed to 23° C. over 1 hour. The volume of the mixture was decreased by half in vacuo, and a 6 N hydrochloric acid aqueous solution (10 mL) was added. An aqueous layer was separated, and then washed with ethyl acetate (10 mL).

Subsequently, the aqueous layer was basified with a saturated sodium carbonate aqueous solution (15 mL), and extracted with ethyl acetate (15 mL×3). A combined organic layer was washed with brine (15 mL), dried with sodium sulfate, filtered, and concentrated under vacuum. A residue was triturated with a solvent mixture of ethyl acetate/diethyl ether (1:1 (v/v)), transferred to an oven-dried 50 mL round bottom flask, and dissolved in N,N-dimethylacetamide (20 mL). N-chlorosuccinimide (334 mg, 2.50 mmol, 0.80 equiv.) was added to the stirred mixture all at once. The mixture was stirred at 23° C. for 12 hours, and then 2,2-dimethylpropanethioamide (293 mg, 2.50 mmol, 0.80 equiv.) was added. The reaction vessel was sealed with a rubber septum, and the mixture was heated to 65° C. and stirred at the same temperature for 16 hours. The reaction mixture was cooled to 23° C., and diluted with water (50 mL) and ethyl acetate (50 mL). The organic layer was separated, and an aqueous layer was extracted with ethyl acetate (50 mL×2). A combined organic layer was continuously washed with water (5 mL) and brine (50 mL), dried with sodium sulfate, filtered, and concentrated under vacuum. A residue was purified with silica gel chromatography while eluting with a solvent mixture of n-hexane/ethyl acetate (100/0 to 0/100 (v/v) thereby obtaining a target compound (S7) as a brown solid (458 mg, yield: 29%).

m.p.: 190-192° C.; $^1$H NMR (500 MHz, $CD_2Cl_2$) δ 9.02 (s, 1H), 8.67 (br s, 1H), 8.36 (d, J=5.4 Hz, 1H), 7.75-7.66 (m, 1H), 7.57-7.47 (m, 1H), 7.44-7.37 (m, 1H), 7.30-7.23 (m, 1H), 7.05-6.95 (m, 2H), 6.88 (d, J=5.4 Hz, 1H), 1.47 (s, 9H); $^{13}$C{$^1$H} NMR (125 MHz, $CD_2Cl_2$) δ 184.1, 160.1 (dd, J=259.0, 3.5 Hz), 159.0, 158.6, 157.1, 151.5 (d, J=248.6 Hz), 146.7, 135.8 (t, J=11.1 Hz), 133.6, 128.5 (d, J=2.2 Hz), 125.6 (d, J=4.3 Hz), 125.3 (d, J=12.8 Hz), 124.4 (d, J=13.8 Hz), 124.1, 117.4 (t, J=15.6 Hz), 117.2, 113.6 (dd, J=23.0, 3.5 Hz), 38.5, 30.8; $^{19}$F NMR (470 MHz, $CD_2Cl_2$) δ −107.7 (d, J=3.5 Hz), −129.2 (t, J=3.5 Hz); IR ($cm^{-1}$): 3171, 3067, 3031, 2966, 2927, 2817, 2763, 1611, 1579, 1464, 1392, 1355, 1276, 1172, 1070, 1002, 895, 845; HRMS (EI): Calculated for $C_{23}H_{19}F_3N_4O_2S_2$ $[M]^+$: 504.0902; Found: 504.0900.

[Preparation Example 8] Preparation of tert-Butyl {3-[1-isopropyl-4-(pyrimidin-4-yl)-1H-pyrazol-3-yl] phenyl}carbamate (S8)

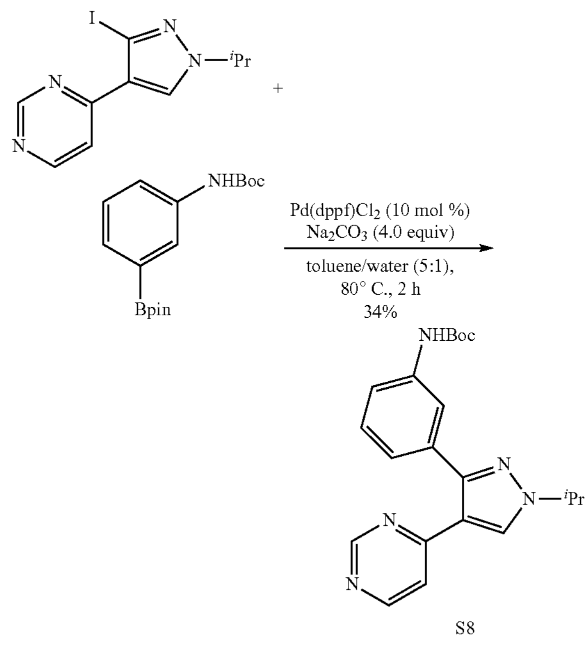

S8

A stirring bar, 4-(3-iodo-1-isopropyl-1H-pyrazol-4-yl)pyrimidine (935 mg, 2.98 mmol, 1.0 equiv.), [3-{(tert-butoxycarbonyl)amino}phenyl]boronic acid pinacol ester (1234 mg, 3.866 mmol, 1.3 equiv.), {1,1'-bis(diphenylphosphino) ferrocene}palladium(II) dichloride (242 mg, 0.296 mmol, 10 mol %), sodium carbonate (1261 mg, 11.90 mmol, 4.0 equiv.), toluene (60 mL), and water (12 mL) were charged into an oven-dried 250 mL round bottom flask equipped with a reflux condenser under argon atmosphere. The mixture was heated to 80° C., and stirred at the same temperature for 2 hours. The reaction mixture was cooled to 23° C., and then diluted with dichloromethane (50 mL) and a saturated sodium bicarbonate aqueous solution (50 mL). An organic layer was separated, and an aqueous layer was extracted with dichloromethane (50 mL×3). A combined organic layer was dried with sodium sulfate, filtered, and concentrated under vacuum. A residue was purified with silica gel chromatography while eluting with a solvent mixture of n-hexane/ethyl acetate (100/0 to 0/100 (v/v)), thereby obtaining a target compound (S8) as an orange solid (384 mg, yield: 34%).

m.p.: 163-165° C.; $^1$H NMR (500 MHz, $CD_2Cl_2$) δ 9.04 (s, 1H), 8.42 (d, J=5.2 Hz, 1H), 8.14 (s, 1H), 7.53 (s, 1H), 7.49 (d, J=7.8 Hz, 1H), 7.31 (dd, J=7.8, 7.8 Hz, 1H), 7.21-7.09 (m, 3H), 4.55 (sept, J=6.6 Hz, 1H), 1.56 (d, J=6.6 Hz, 6H), 1.48 (s, 9H); $^{13}$C{$^1$H} NMR (150 MHz, $CD_2Cl_2$) δ 159.9, 159.2, 156.8, 153.1, 150.2, 139.5, 134.8, 129.7, 129.4, 123.8, 119.2, 118.6, 118.2(5), 118.2(1), 80.6, 54.8, 28.4, 23.0; IR ($cm^{-1}$): 3239, 3038, 2975, 2932, 2874, 1722, 1581, 1390, 1365, 1236, 1154, 1055, 851; HRMS (EI): Calculated for $C_{21}H_{25}N_5O_2$ $[M]^+$: 379.2008; Found: 379.2006.

[Preparation Example 9] Preparation of N-tosyl-ruxolitinib (S9)

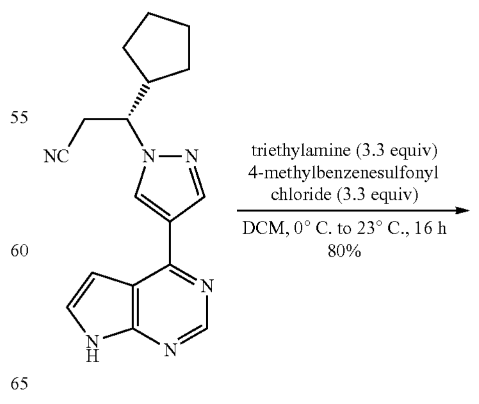

-continued

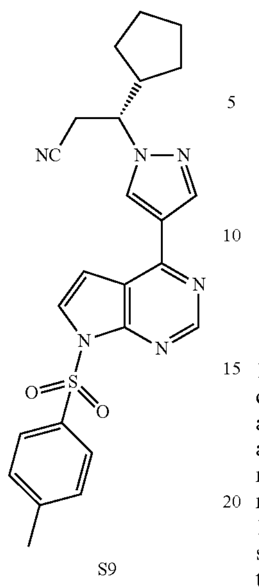

S9

A stirring bar, ruxolitinib (1022 mg, 3.336 mmol, 1.0 equiv.), and anhydrous dichloromethane (15 mL) were charged into an oven-dried 50 mL round bottom flask under argon atmosphere. Triethylamine (1.53 mL, 1.11 g, 11.0 mmol, 3.3 equiv.) was added to the stirred mixture through a syringe, the mixture was cooled to 0° C., and then 4-methylbenzenesulfonyl chloride (2099 mg, 11.01 mmol, 3.3 equiv.) was added. The mixture was warmed to 23° C. over 5 minutes, and then stirred at the same temperature for 16 hours. Dichloromethane (50 mL) and a saturated ammonium chloride aqueous solution (50 mL) were added, and an organic layer was separated. An aqueous layer was extracted with dichloromethane (50 mL×2). A combined organic layer was dried with sodium sulfate, filtered, and concentrated under vacuum. A residue was purified with silica gel chromatography while eluting with a solvent mixture of dichloromethane/methanol (100/0 to 90/10 (v/v)), thereby obtaining a target compound (S9) as a brown solid (1.23 g, yield: 80%).

m.p.: 72-74° C.; $^{1}$H NMR (400 MHz, $CD_2Cl_2$) δ 8.86 (s, 1H), 8.27 (s, 1H), 8.23 (s, 1H), 8.10-8.02 (m, 2H), 7.78 (d, J=4.1 Hz, 1H), 7.35-7.30 (m, 2H), 6.88 (d, J=4.1 Hz, 1H), 4.25 (ddd, J=9.8, 8.9, 3.9 Hz, 1H), 3.11 (dd, J=17.0, 8.9 Hz, 1H), 2.93 (dd, J=17.0, 3.9 Hz, 1H), 2.62-2.47 (m, 1H), 2.38 (s, 3H), 1.99-1.89 (m, 1H), 1.76-1.56 (m, 3H), 1.55-1.44 (m, 2H), 1.35-1.13 (m, 2H); $^{13}C\{^{1}H\}$ NMR (100 MHz, $CD_2Cl_2$) δ 153.5, 152.4, 152.3, 146.5, 140.2, 135.2, 130.7, 130.2, 128.6, 126.9, 121.1, 117.2, 116.2, 104.1, 64.8, 44.8, 30.4, 30.3, 25.8, 25.2, 23.9, 21.8; IR ($cm^{-1}$): 3138, 3117, 3050, 2950, 2868, 2251, 1577, 1348, 1175, 1146, 1087, 981, 903, 809; HRMS (ESI): Calculated for $C_{24}H_{24}N_6O_2S$ $[M]^+$: 460.1681; Found: 460.1679.

[Example 1] Synthesis and Separation of Reaction Intermediate (1)

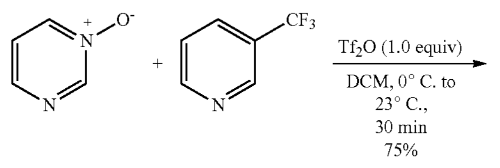

-continued

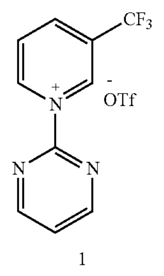

1

A stirring bar, pyrimidine N-oxide (192 mg, 2.00 mmol, 1.0 equiv.), and anhydrous dichloromethane (10.0 mL) were charged into an oven-dried 100 mL round bottom flask under argon atmosphere. The stirred solution was cooled to 0° C., and then 3-(trifluoromethyl)pyridine (462 μL, 590 mg, 4.00 mmol, 2.0 equiv.) was added through a syringe. Trifluoromethanesulfonic anhydride (337 μL, 565 mg, 2.00 mmol, 1.0 equiv.) was added dropwise through a syringe while stirring at 0° C., and rapid precipitation was observed at this time. The mixture was warmed to 23° C. over 5 minutes, and then stirred at the same temperature for 30 minutes. The reaction mixture was filtered on a glass frit, and a residue was washed with ethyl acetate (5 mL×3) to obtain 560 mg of Intermediate 1 as a light yellow solid (yield: 75%).

m.p.: 199-201° C.; $^{1}$H NMR (400 MHz, $(CD_3)_2CO$) δ 10.64-10.61 (m, 1H), 10.61-10.58 (m, 1H), 9.51 (d, J=8.0 Hz, 1H), 9.32 (d, J=4.8 Hz, 2H), 8.87 (dd, J=7.2, 7.2 Hz, 1H), 8.10 (t, J=4.8 Hz, 1H); $^{13}C\{^{1}H\}$ NMR (125 MHz, $CD_3CN$) δ 161.6, 155.4, 148.3 (q, J=3.0 Hz), 145.5, 140.0, 131.6 (q, J=36.9 Hz), 130.7, 125.8, 122.4 (q, J=272.6 Hz), 122.1 (q, J=320.9 Hz); $^{19}$F NMR (470 MHz, $CD_3CN$) δ −63.5, −79.3; IR ($cm^{-1}$): 3102, 1645, 1602, 1561, 1398, 1333, 1251, 1144, 1092, 1024, 831; HRMS (FAB): Calculated for $C_{10}H_7F_3N_3$ $[M]^+$: 226.0587; Found: 226.0588.

Example II: Amination of N-heteroarene

Procedure A: Use of Electron-Deficient Pyridine Derivative

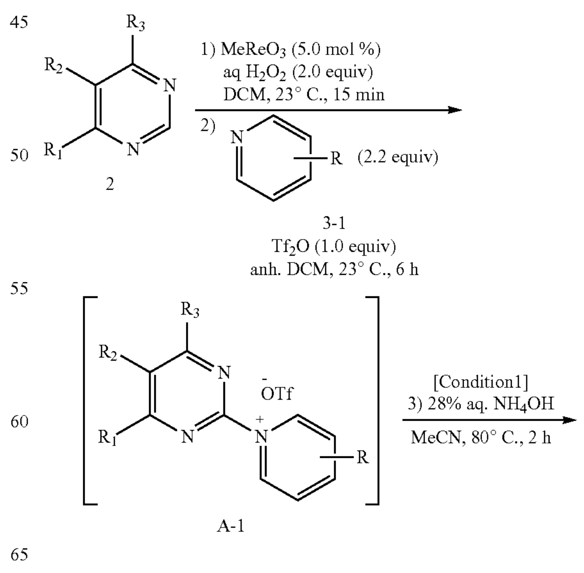

2

3-1

A-1

-continued

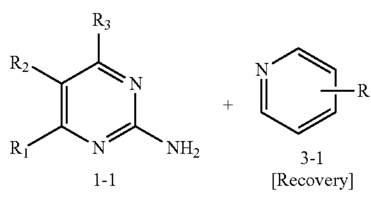

1-1

3-1 [Recovery]

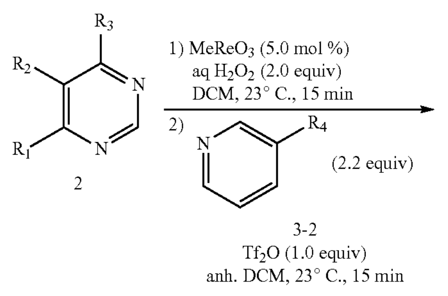

2

3-2

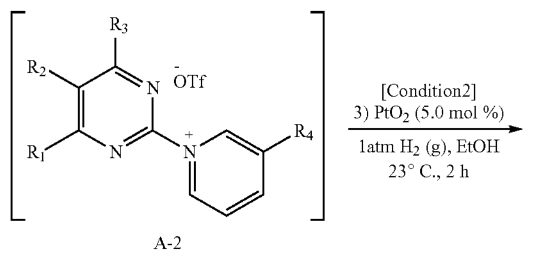

A-2

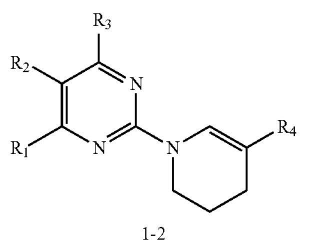

1-2

Step 1:

A pyrimidine compound (Chemical Formula 2, 0.25 mmol, 1.0 equiv.) and dichloromethane (0.20 mL) were added to a 4 mL vial equipped with a stirrer bar, and methyltrioxorhenium(VII) ($MeReO_3$) (3.1 mg, 0.012 mmol, 5.0 mol %) was added with stirring. A 50% hydrogen peroxide aqueous solution (28 μL, 34 mg, 0.50 mmol, 2.0 equiv.) was added dropwise through a syringe while stirring at 23° C., and the vial was sealed with a plastic cap. Stirring was performed at 23° C. for 6 hours, the reaction mixture was diluted with dichloromethane (2 mL), dried with sodium sulfate, filtered on cotton, added to a 50 mL round bottom flask, and concentrated under vacuum. A stirring bar was added to the flask, and a residue was dried for 2 hours under reduced pressure and then placed under argon.

Step 2:

Anhydrous dichloromethane (5.00 mL) was added to the reaction vessel under argon, and a pyrimidine compound (Chemical Formula 3-1 or 3-2, 0.55 mmol, 2.2 equiv.) was added dropwise through a syringe while stirring at 23° C. Subsequently, trifluoromethanesulfonic anhydride (44 μL, 74 mg, 0.26 mmol, 1.0 equiv.) was added dropwise through a syringe. Stirring was performed at 23° C. for 15 minutes under argon, and the reaction mixture was transferred to a 20 mL vial and subsequently concentrated under vacuum.

Step 3: For amination, the reaction mixture of step 2 was applied to two different conditions.

[Condition 1]

Acetonitrile (1.25 mL) was added to the residue of step 2, and then 28% ammonia water (1.69 mL, 1.52 g, 25.0 mmol, 100 equiv.) was added through a syringe while stirring at 23° C. The vial was sealed with a black cap and a Teflon tape, and then heated to 80° C. Stirring was performed at the same temperature for 2 hours, and then the reaction mixture was cooled to 23° C. and concentrated in vacuum. Crude heteroarylamine was purified with silica gel chromatography eluting with dichloromethane/methanol (100/0 to 90/10(v/v)) to obtain a pyrimidin-2-amine compound (Chemical Formula 1-1) which was a desired product.

**When 3-benzoylpyridine was used as an amination reagent, the reagent was able to be recovered in chromatography separation.

[Condition 2]

The residue of step 2 was dried for 1 hour under reduced pressure, and then anhydrous ethanol (1.25 mL) and $PtO_2$ (2.9 mg, 0.013 mmol, 5.0 mol %) were added. The reaction mixture was stirred at 23° C. for 2 hours under $H_2$ atmosphere, and then filtered with a short pad of celite and concentrated under vacuum. Dichloromethane (20 mL) was added to the residue, and the mixture was washed with a saturated sodium bicarbonate aqueous solution (20 mL). An aqueous layer was extracted with dichloromethane (20 mL×2). A combined organic layer was dried with sodium sulfate, filtered, and concentrated under vacuum. A crude residue was purified with silica gel chromatography eluting with n-hexane/dichloromethane (100/0 to 80/20 (v/v)) to obtain a cyclic (2-enamino)pyrimidine compound (Chemical Formula 1-2) which was a desired product.

Procedure B: Use of Imidoyl Chloride

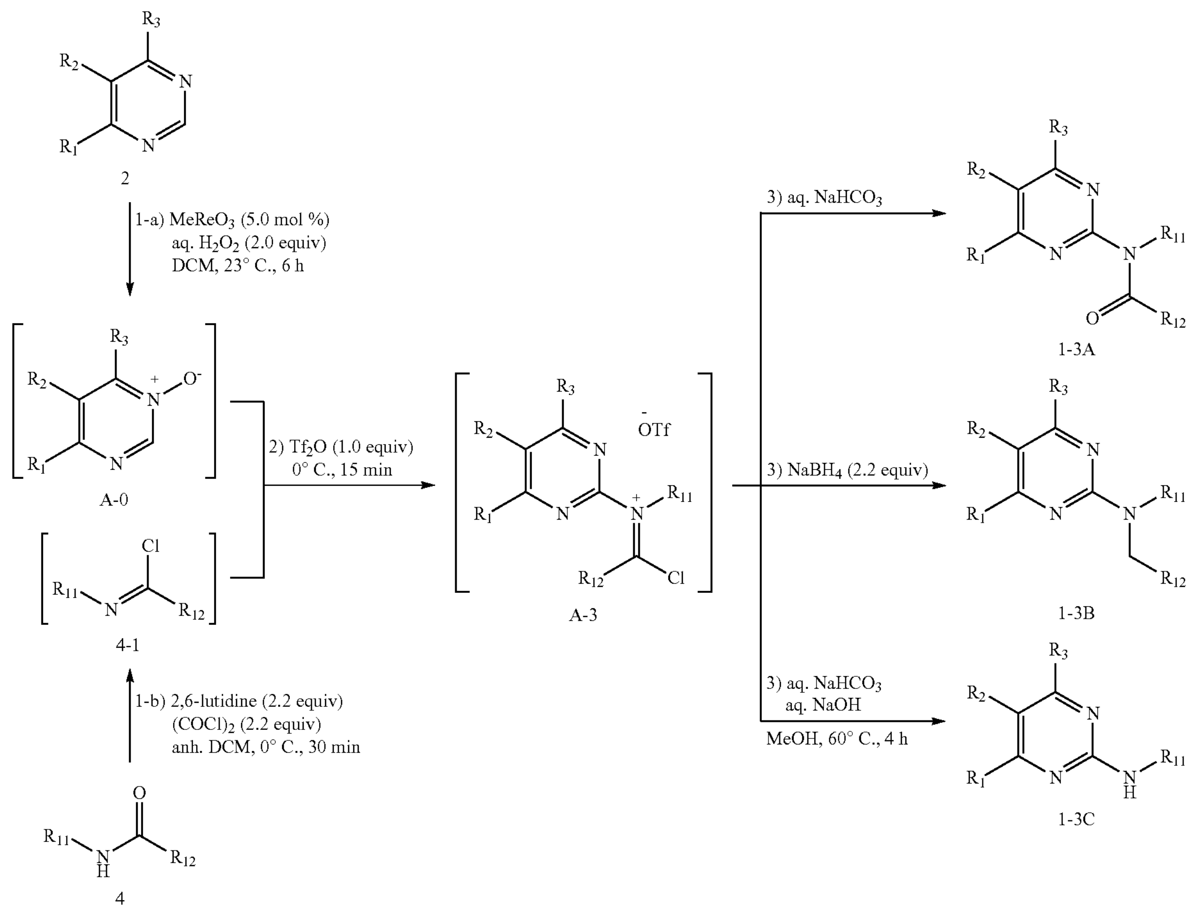

Step 1-a:

Heteroarene substrate (0.25 mmol, 1.0 equiv.) and dichloromethane (0.20 mL) were added to a 4 mL vial equipped with a stirrer bar, and methyltrioxorhenium(VII) ($MeReO_3$) (3.1 mg, 0.012 mmol, 5.0 mol %) was added with stirring. A 50% hydrogen peroxide aqueous solution (28 μL, 34 mg, 0.50 mmol, 2.0 equiv.) was added dropwise through a syringe while stirring at 23° C., and the vial was sealed with a plastic cap. Stirring was performed at 23° C. for 6 hours, the reaction mixture was diluted with dichloromethane (2 mL), dried with sodium sulfate, filtered on cotton, added to a 50 mL round bottom flask, and concentrated under vacuum. A stirring bar was added to the flask, and a residue was dried for 2 hours under reduced pressure and then placed under argon. Anhydrous dichloromethane (2.5 mL) was added to the reaction vessel under argon, and then the mixture was cooled to 0° C. (Mixture A).

Step 1-b:

A secondary amide substrate (0.55 mmol, 2.2 equiv.) and anhydrous dichloromethane (2.75 mL) were added to an oven-dried 20 mL vial equipped with a stirrer bar under argon, and then the mixture was cooled to 0° C. While stirring, 2,6-lutidine (64 μL, 59 mg, 0.55 mmol, 2.2 equiv.) and oxalyl chloride (46 μL, 70 mg, 0.55 mmol, 2.2 equiv.) were continuously added dropwise through a syringe. Gassing was observed immediately after adding oxalyl chloride. Subsequently, the mixture was stirred at 0° C. for 30 minutes (Mixture B).

Step 2:

Mixture B was transferred to a flask including Mixture A through a syringe. Subsequently, trifluoromethanesulfonic anhydride (44 μL, 74 mg, 0.26 mmol, 1.0 equiv.) was added dropwise at 0° C. through a syringe. The mixture was stirred at 0° C. for 15 minutes under argon.

Step 3: For amination, the reaction mixture of step 2 was applied to three different conditions.

[Condition 1]

The reaction mixture of step 2 was diluted with dichloromethane (20 mL) and a saturated sodium bicarbonate aqueous solution (20 mL), and warmed to 23° C. An organic layer was separated, and an aqueous layer was extracted with dichloromethane (20 mL×2). A combined organic layer was dried with sodium sulfate, filtered, and concentrated under vacuum. Crude heteroarylamine was purified with silica gel chromatography to obtain a pyrimidin-2-substituted amine compound (Chemical Formula 1-3A) which was a desired product.

[Condition 2]

The reaction mixture of step 2 was concentrated at 0° C. under reduced pressure. Anhydrous acetonitrile (5.0 mL) and sodium borohydride (21 mg, 0.55 mmol, 2.2 equiv.) were added to a residue. The reaction vessel was sealed, and the mixture was heated to 60° C. Stirring was performed at the same temperature for 4 hours, and the reaction mixture was cooled to 23° C. and diluted with dichloromethane (20 mL) and a saturated sodium bicarbonate aqueous solution (20 mL). An organic layer was separated, and an aqueous layer was extracted with dichloromethane (20 mL×2). A combined organic layer was dried with sodium sulfate, filtered, and concentrated under vacuum. Crude heteroarylamine was purified with silica gel chromatography to obtain a pyrimidin-2-substituted amine compound (Chemical Formula 1-3B) which was a desired product.

[Condition 3]

The reaction mixture of step 2 was diluted with a saturated sodium bicarbonate aqueous solution (5 mL), and warmed to 23° C. An organic layer was separated, and then an aqueous layer was extracted with dichloromethane (5 mL×2). The combined organic layer was concentrated under vacuum. Methanol (1.25 mL) and a 2 N sodium hydroxide aqueous solution (1.25 mL) were added to a residue. The vial was sealed with a black cap and a Teflon tape, and then heated to 60° C. Stirring was performed at the same temperature for 4 hours, and the reaction mixture was cooled to 23° C. and diluted with dichloromethane (20 mL) and water (20 mL). An organic layer was separated, and an aqueous layer was extracted with dichloromethane (20 mL×2). A combined organic layer was dried with sodium sulfate, filtered, and concentrated under vacuum. Crude heteroarylamine was purified with silica gel chromatography to obtain a pyrimidin-2-substituted amine compound (Chemical Formula 1-3C) which was a desired product.

The format of the properties of the products prepared using the 2-amination method of pyrimidine described above is as follows: [Structure of synthesized compound] [Used procedures] [Used imine-type reagent] [Yield and identification data].

[Example 2] Preparation of 4-phenylpyrimidin-2-amine (2)

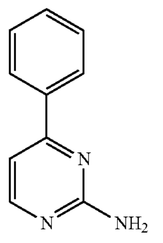 [SMILES: Nc1nccc(-c2ccccc2)n1]

[Procedure A, Condition 1] [3-benzoylpyridine]

Yellow solid (34 mg, 80% yield); m.p.: 157-159° C.; $^{1}H$ NMR (500 MHz, $CD_2Cl_2$) δ 8.33 (d, J=5.2 Hz, 1H), 8.05-8.00 (m, 2H), 7.50-7.44 (m, 3H), 7.07 (d, J=5.2 Hz, 1H), 5.21 (br s, 2H); $^{13}C\{^{1}H\}$ NMR (125 MHz, $CD_2Cl_2$) δ 165.4, 163.9, 159.2, 137.6, 130.9, 129.1, 127.3, 107.9; IR ($cm^{-1}$): 3308, 3140, 3117, 2960, 2929, 2873, 2809, 2702, 1649, 1550, 1450, 1211, 818; HRMS (ESI): Calculated for $C_{10}H_{10}N_3$ $[M+H]^+$: 172.0869; Found: 172.0867.

After separation with chromatography, 94 mg of 3-benzoylpyridine (recovery yield: 94%) was obtained.

[Example 3] Preparation of 4-phenyl-2-[5-(trifluoromethyl)-3,4-dihydropyridin-1(2H)-yl]pyrimidine (3)

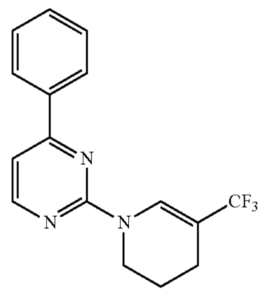 [SMILES: FC(F)(F)C1=CN(c2nccc(-c3ccccc3)n2)CCC1]

[Procedure A, Condition 2] [3-(trifluoromethyl)pyridine]

White solid (27 mg, 36% yield); m.p.: 98-100° C.; $^{1}H$ NMR (500 MHz, $CD_2Cl_2$) δ 8.49 (d, J=5.2 Hz, 1H), 8.36 (s, 1H), 8.15-8.07 (m, 2H), 7.57-7.47 (m, 3H), 7.24 (d, J=5.2 Hz, 1H), 4.07-3.97 (m, 2H), 2.31 (t, J=5.9 Hz, 2H), 2.04 (p, J=5.9 Hz, 2H); $^{13}C\{^{1}H\}$ NMR (125 MHz, $CD_2Cl_2$) δ 164.9, 159.1, 158.9, 137.2, 131.4, 129.2, 129.0 (q, J=7.3 Hz), 127.4, 126.1 (q, J=268.1 Hz), 109.3, 104.2 (q, J=31.2 Hz), 42.3, 21.3, 20.0; $^{19}F$ NMR (376 MHz, $CD_2Cl_2$) δ −65.9; IR ($cm^{-1}$) 3106, 3059, 2990, 2955, 2922, 2879, 2855, 1672, 1552, 1460, 1361, 1319, 1273, 1209, 1160, 1141, 1078, 1043, 989, 920, 880, 830; HRMS (EI): Calculated for $C_{16}H_{14}F_3N_3$ $[M]^+$: 305.1140; Found: 305.1137.

[Example 4] Preparation of N-allyl-N-(4-phenylpyrimidin-2-yl)acetamide (4)

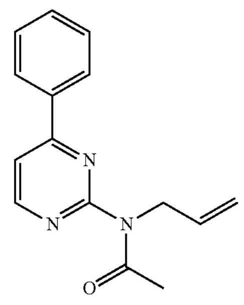 [SMILES: C=CCN(C(C)=O)c1nccc(-c2ccccc2)n1]

[Procedure B, Condition 1] [N-acetylallylamine]

White solid (58 mg, 91% yield); m.p.: 68-70° C.; $^{1}H$ NMR (500 MHz, $CD_2Cl_2$) δ 8.66 (d, J=5.2 Hz, 1H), 8.14-8.08 (m, 2H), 7.56-7.50 (m, 3H), 7.49 (d, J=5.2 Hz, 1H), 6.01-5.91 (m, 1H), 5.22-5.14 (m, 1H), 5.10-5.05 (m, 1H), 4.80-4.74 (m, 2H), 2.51 (s, 3H); $^{13}C\{^{1}H\}$ NMR (125 MHz, $CD_2Cl_2$) δ 172.1, 165.1, 161.5, 158.9, 136.7, 134.6, 131.7, 129.4, 127.5, 116.2, 112.5, 48.4, 26.0; IR ($cm^{-1}$): 3078, 2963, 963, 1653, 1572, 1550, 1420, 1396, 1368, 1344, 1305, 1267, 1238, 1150, 1116, 1017, 976, 928, 891, 853; HRMS (EI): Calculated for $C_{15}H_{15}N_3O$ $[M]^+$: 253.1215; Found: 253.1211.

[Example 5] Preparation of N-benzyl-N-methyl-4-phenylpyrimidin-2-amine (5)

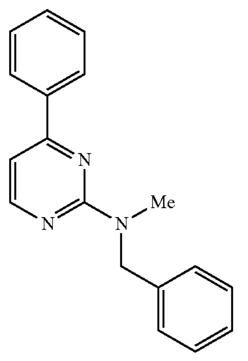 [SMILES: CN(Cc1ccccc1)c1nccc(-c2ccccc2)n1]

[Procedure B, Condition 2] [N-methylbenzamide]

Opaque oil (44 mg, 65% yield); $^1$H NMR (500 MHz, $CD_2Cl_2$) δ 8.39 (d, J=5.1 Hz, 1H), 8.12-8.05 (m, 2H), 7.50-7.44 (m, 3H), 7.34-7.28 (m, 4H), 7.28-7.21 (m, 1H), 6.99 (d, J=5.1 Hz, 1H), 5.00 (s, 2H), 3.22 (s, 3H); $^{13}C\{^1H\}$ NMR (125 MHz, $CD_2Cl_2$) δ 164.4, 162.9, 158.8, 139.4, 138.2, 130.8, 129.0, 128.8, 127.7, 127.3, 127.2(7), 105.5, 52.7, 35.2; IR ($cm^{-1}$): 3060, 3026, 2922, 2853, 1587, 1549, 1510, 1450, 1403, 1346, 1001, 817; HRMS (EI): Calculated for $C_{18}H_{17}N_3$ $[M]^+$: 275.1422; Found: 275.1423.

[Example 6] Synthesis of N-methyl-4-phenylpyrimidin-2-amine (6)

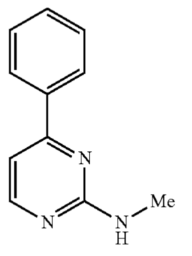 [SMILES: CNc1nccc(-c2ccccc2)n1]

[Procedure B, Condition 3] [N-methylacetamide]

White solid (41.7 mg, 90% yield); m.p.: 93-95° C.; $^1$H NMR (500 MHz, $CD_2Cl_2$) δ 8.33 (d, J=5.1 Hz, 1H), 8.12-8.00 (m, 2H), 7.51-7.44 (m, 3H), 6.99 (d, J=5.1 Hz, 1H), 5.26 (br s, 1H), 3.05 (d, J=5.0 Hz, 3H); $^{13}C\{^1H\}$ NMR (125 MHz, $CD_2Cl_2$) δ 164.8, 163.8, 159.0, 138.0, 130.8, 129.0, 127.3, 106.6, 28.6.

[Example 7] Preparation of N,4-diphenylpyrimidin-2-amine (7)

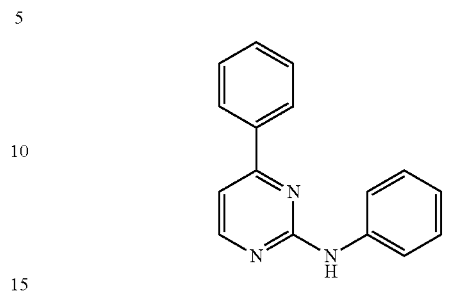

[Procedure B, Condition 3] [acetanilide]

White solid (53.8 mg, 87% yield); m.p.: 123-125° C.; $^1$H NMR (500 MHz, $CD_2Cl_2$) δ 8.48 (d, J=5.2 Hz, 1H), 8.14-8.07 (m, 2H), 7.77-7.71 (m, 2H), 7.55-7.48 (m, 3H), 7.41-7.29 (m, 3H), 7.21 (d, J=5.2 Hz, 1H), 7.07-7.03 (m, 1H); $^{13}C\{^1H\}$ NMR (125 MHz, $CD_2Cl_2$) δ 165.1, 160.8, 159.0, 140.3, 137.5, 131.2, 129.2(3), 129.2(1), 127.4, 122.6, 119.5, 108.8; IR ($cm^{-1}$): 3249, 3088, 3031, 2972, 2887, 2851, 1598, 1565, 1537, 1468, 1444, 1392, 1324, 1066, 814.

[Example 8] Preparation of N-benzyl-4-phenylpyrimidin-2-amine (8)

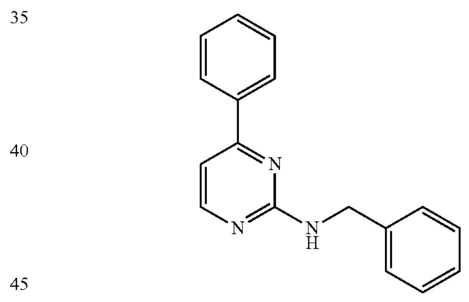

[Procedure B, Condition 3] [N-benzylacetamide]

White solid (32.7 mg, 50% yield); m.p.: 126-128° C.; $^1$H NMR (500 MHz, $CD_2Cl_2$) δ 8.32 (d, J=5.1 Hz, 1H), 8.09-8.00 (m, 2H), 7.51-7.43 (m, 3H), 7.43-7.37 (m, 2H), 7.37-7.30 (m, 2H), 7.30-7.23 (m, 1H), 7.02 (d, J=5.1 Hz, 1H), 5.77 (br s, 1H), 4.72 (d, J=6.0 Hz, 2H); $^{13}C\{^1H\}$ NMR (125 MHz, $CD_2Cl_2$) δ 164.9, 163.1, 159.1, 140.3, 137.8, 130.9, 129.0, 128.9, 127.8, 127.4, 127.3, 107.1, 45.7; IR ($cm^{-1}$): 3247, 3061, 3028, 2947, 2897, 2851, 1588, 1564, 1493, 1444, 1408, 1352, 1324, 1133, 1067, 1027, 815.

[Example 9] Preparation of 4-phenyl-N-(2,2,2-trifluoroethyl)pyrimidin-2-amine (9)

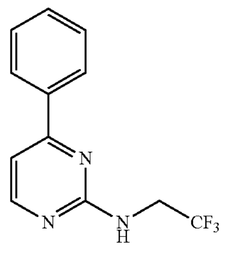 [SMILES: FC(F)(F)CNc1nccc(-c2ccccc2)n1]

[Procedure B, Condition 3] [S1]

White solid (9.5 mg, 15% yield); m.p.: 163-165° C.; $^{1}$H NMR (500 MHz, $CD_2Cl_2$) δ 8.39 (d, J=5.1 Hz, 1H), 8.09-8.02 (m, 2H), 7.53-7.45 (m, 3H), 7.14 (d, J=5.1 Hz, 1H), 5.54 (br s, 1H), 4.33-4.23 (m, 2H); $^{13}$C{$^{1}$H} NMR (125 MHz, $CD_2Cl_2$) δ 165.2, 162.3, 159.2, 137.4, 131.2, 129.1, 127.4, 125.4 (q, J=279 Hz), 108.5, 43.1 (q, J=34.1 Hz); $^{19}$F NMR (376 MHz, $CD_2Cl_2$) δ −73.2; IR ($cm^{-1}$): 3248, 3118, 3087, 3060, 2984, 1567, 1461, 1440, 1420, 1328, 1261, 1137, 959, 821; HRMS (EI): Calculated for $C_{12}H_{10}F_3N_3$ $[M]^+$: 253.0827; Found: 253.0824.

[Example 10] Preparation of N-cyclopropyl-4-phenylpyrimidin-2-amine (10)

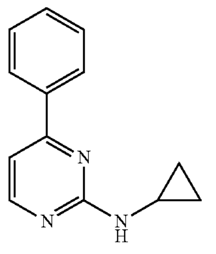 [SMILES: c1ccc(-c2ccnc(NC3CC3)n2)cc1]

[Procedure B, Condition 3] [N-cyclopropyl-2-phenylacetamide]

White solid (36 mg, 69% yield); m.p.: 118-120° C.; $^{1}$H NMR (500 MHz, $CD_2Cl_2$) δ 8.36 (d, J=5.1 Hz, 1H), 8.12-8.01 (m, 2H), 7.52-7.44 (m, 3H), 7.04 (d, J=5.1 Hz, 1H), 5.53 (br s, 1H), 2.89-2.81 (m, 1H), 0.87-0.77 (m, 2H), 0.61-0.52 (m, 2H); $^{13}$C{$^{1}$H} NMR (125 MHz, $CD_2Cl_2$) δ 164.8, 164.2, 159.0, 137.9, 130.8, 129.0, 127.3, 107.2, 24.4, 7.4; IR ($cm^{-1}$): 3227, 3107, 3051, 3033, 2973, 1561, 1528, 1438, 1413, 1356, 1324, 1208, 1069, 1018, 823.

[Example 11] Preparation of N-(bicyclo[1.1.1]pentan-1-yl)-4-phenylpyrimidin-2-amine (11)

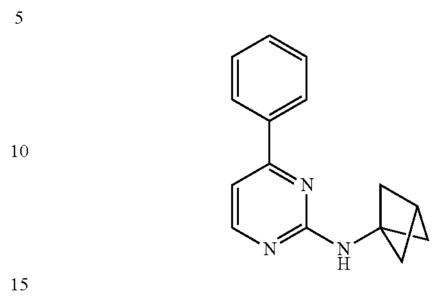

[Procedure B, Condition 3] [N-(bicyclo[1.1.1]pentan-1-yl)acetamide]

White solid (40 mg, 67% yield); m.p.: 198-200° C.; $^{1}$H NMR (500 MHz, $CD_2Cl_2$) δ 8.31 (d, J=5.2 Hz, 1H), 8.10-8.03 (m, 2H), 7.51-7.45 (m, 3H), 7.04 (d, J=5.2 Hz, 1H), 5.72 (br s, 1H), 2.51 (s, 1H), 2.21 (s, 6H); $^{13}$C{$^{1}$H} NMR (125 MHz, $CD_2Cl_2$) δ 164.7, 163.0, 159.0, 137.9, 130.8, 129.1, 127.3, 107.2, 52.8, 50.4, 25.3; IR ($cm^{-1}$): 3219, 3159, 3097, 3041, 2973, 2911, 2868, 1555, 1525, 1434, 1410, 1322, 1276, 1203, 993, 824; HRMS (FAB): Calculated for $C_{15}H_{16}N_3[M+H]^+$: 238.1339; Found: 238.1347.

[Example 12] Preparation of N-[1-(4-fluorophenyl)cyclopropyl]-4-phenylpyrimidin-2-amine (12)

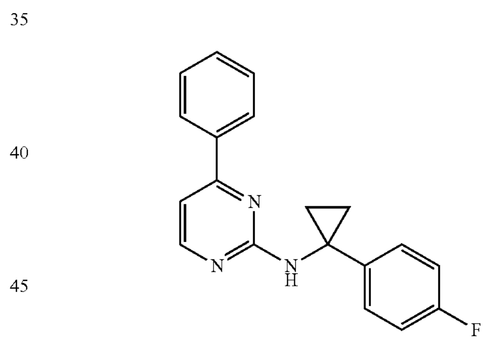

[Procedure B, Condition 3] [S2]

Slightly yellow solid (60 mg, 79% yield); m.p.: 129-131° C.; $^{1}$H NMR (600 MHz, $CD_2Cl_2$) δ 8.33 (d, J=5.1 Hz, 1H), 8.03-7.96 (m, 2H), 7.49-7.42 (m, 3H), 7.40-7.25 (br s, 2H), 7.04 (d, J=5.1 Hz, 1H), 6.98-6.92 (m, 2H), 6.14 (br s, 1H), 1.38-1.32 (m, 4H); $^{13}$C{$^{1}$H} NMR (150 MHz, $CD_2Cl_2$) δ 164.9 (br), 163.2, 161.6 (d, J=243.4 Hz), 159.0, 140.3 (d, J=2.9 Hz), 137.8, 130.9, 129.1, 127.6 (br), 127.3, 115.1 (d, J=21.3 Hz), 107.6 (br), 35.8, 19.3; $^{19}$F NMR (564 MHz, $CD_2Cl_2$) δ −118.5; IR ($cm^{-1}$): 3219, 3060, 3034, 3013, 2970, 2929, 1562, 1508, 1435, 1407, 1278, 1218, 1153, 1024, 836, 813; HRMS (EI): Calculated for $C_{19}H_{16}FN_3$ $[M]^+$: 305.1328; Found: 305.1324.

[Example 13] Preparation of N-(3,3-difluorocyclobutyl)-4-phenylpyrimidin-2-amine (13)

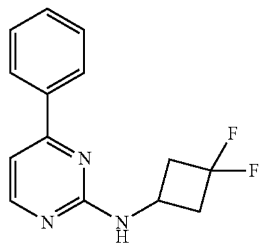 [SMILES: FC1(F)CC(Nc2nccc(-c3ccccc3)n2)C1]

[Procedure B, Condition 3] [S3]

White solid (31 mg, 47% yield); m.p.: 159-161° C.; $^1$H NMR (500 MHz, $CD_2Cl_2$) δ 8.35 (d, J=5.1 Hz, 1H), 8.11-8.01 (m, 2H), 7.54-7.45 (m, 3H), 7.08 (d, J=5.1 Hz, 1H), 5.83 (br s, 1H), 4.49-4.33 (m, 1H), 3.17-3.00 (m, 2H), 2.67-2.48 (m, 2H); $^{13}C\{^1H\}$ NMR (125 MHz, $CD_2Cl_2$) δ 165.0, 162.5, 159.0, 137.6, 131.1, 129.1, 127.3, 119.9 (dd, J=282.1, 270.5 Hz), 107.6, 43.6 (dd, J=23.1, 21.3 Hz), 36.9 (dd, J=17.8, 6.7 Hz); $^{19}F$ NMR (470 MHz, $CD_2Cl_2$) δ −84.3 (d, J=196.9 Hz), −97.7 (d, J=197.0 Hz); IR ($cm^{-1}$): 3259, 3088, 2993, 1566, 1535, 1422, 1284, 1234, 1156, 1057, 889, 820; HRMS (EI): Calculated for $C_{14}H_{13}F_2N_3$ $[M]^+$: 261.1078; Found: 261.1075.

[Example 14] Preparation of pyrimidin-2-amine (14)

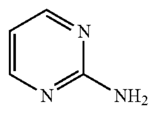

[Procedure A, Condition 1] [3-benzoylpyridine]

White solid (16 mg, 67% yield); m.p.: 125-127° C.; $^1$H NMR (500 MHz, $CD_3CN$) δ 8.24 (d, J=4.8 Hz, 2H), 6.59 (t, J=4.8 Hz, 1H), 5.47 (br s, 2H); $^{13}C\{^1H\}$ NMR (125 MHz, $CD_3CN$) δ 164.7, 159.2, 112.0; IR ($cm^{-1}$): 3324, 3159. 2955, 2922, 2852, 2778, 2681, 1644, 1555, 1471, 1355, 1222, 800.

After separation with chromatography, 88 mg of 3-benzoylpyridine (recovery yield: 87%) was obtained.

[Example 15] Preparation of 4-cyclohexylpyrimidin-2-amine (15)

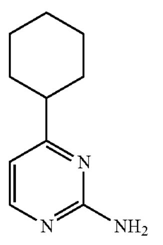 [SMILES: Nc1nccc(C2CCCCC2)n1]

[Procedure A, Condition 1] [3-benzoylpyridine]

White solid (23 mg, 52% yield); m.p.: 104-106° C.; $^1$H NMR (500 MHz, $CD_2Cl_2$) δ 8.14 (d, J=5.1 Hz, 1H), 6.48 (d, J=5.1 Hz, 1H), 4.91 (br s, 2H), 2.47-2.40 (m, 1H), 1.90-1.78 (m, 4H), 1.76-1.69 (m, 1H), 1.49-1.31 (m, 4H), 1.30-1.22 (m, 1H); $^{13}C\{^1H\}$ NMR (125 MHz, $CD_2Cl_2$) δ 176.4, 163.5, 158.4, 109.3, 46.4, 32.3, 26.7, 26.4; IR ($cm^{-1}$): 3332, 3305, 3164, 2925, 2852, 1636, 1558, 1471, 1346, 1260, 1207, 806; HRMS (EI): Calculated for $C_{10}H_{15}N_3$ $[M]^+$: 177.1266; Found: 177.1264.

After separation with chromatography, 96 mg of 3-benzoylpyridine (recovery yield: 95%) was obtained.

[Example 16] Preparation of 4-methoxypyrimidin-2-amine (16)

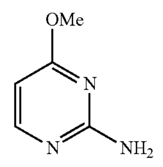

[Procedure A, Condition 1] [3-benzoylpyridine]

Yellow solid (22 mg, 70% yield); m.p.: 108-110° C.; $^1$H NMR (500 MHz, $CD_2Cl_2$) δ 7.97 (d, J=5.7 Hz, 1H), 6.05 (d, J=5.7 Hz, 1H), 5.28 (br s, 2H), 3.85 (s, 3H); $^{13}C\{^1H\}$ NMR (125 MHz, $CD_2Cl_2$) δ 170.9, 163.6, 158.4, 98.3, 53.5; IR ($cm^{-1}$): 3439, 3319, 3150, 3130, 3084, 3011, 2998, 2957, 2861, 2794, 2733, 1649, 1564, 1461, 1340, 1294, 1240, 1023, 908, 804; HRMS (ESI): Calculated for $C_5H_8N_3O$ $[M+H]^+$: 126.0662; Found: 126.0667.

After separation with chromatography, 96 mg of 3-benzoylpyridine (recovery yield: 95%) was obtained.

[Example 17] Preparation of 4,6-dimethylpyrimidin-2-amine (17)

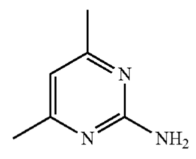

[Procedure A, Condition 1] [3-benzoylpyridine]

Yellow solid (17 mg, 55% yield); m.p.: 143-145° C.; $^1$H NMR (500 MHz, $CD_2Cl_2$) δ 6.38 (s, 1H), 4.91 (br s, 2H), 2.25 (s, 6H); $^{13}C\{^1H\}$ NMR (125 MHz, $CD_2Cl_2$) δ 168.2, 163.3, 110.8, 23.9; IR ($cm^{-1}$): 3396, 3307, 3151, 2917, 1627, 1561, 1459, 1367, 951.

After separation with chromatography, 95 mg of 3-benzoylpyridine (recovery yield: 94%) was obtained.

[Example 18] Preparation of 2-(2-aminopyrimidin-4-yl)ethan-1-ol (18)

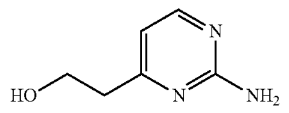

[Procedure A, Condition 1] [3-benzoylpyridine]

White solid (14 mg, 39% yield); m.p.: 103-105° C.; $^{1}H$ NMR (500 MHz, $CD_2Cl_2$) δ 8.16 (d, J=5.0 Hz, 1H), 6.50 (d, J=5.0 Hz, 1H), 5.05 (br s, 2H), 3.90 (t, J=5.5 Hz, 2H), 3.54 (br s, 1H), 2.79 (t, J=5.5 Hz, 2H); $^{13}C\{^{1}H\}$ NMR (125 MHz, $CD_2Cl_2$) δ 170.6, 163.1, 158.7, 111.4, 61.1, 39.2; IR ($cm^{-1}$): 3330, 3164, 2956, 2912, 2883, 2759, 2659, 1663, 1561, 1427, 1347, 1184, 1054, 868; HRMS (EI): Calculated for $C_6H_9N_3O$ $[M]^+$: 139.0746; Found: 139.0743.

After separation with chromatography, 90 mg of 3-benzoylpyridine (recovery yield: 89%) was obtained.

[Example 19] Preparation of 4-{2-[(triisopropylsilyl)oxy]ethyl}pyrimidin-2-amine (19)

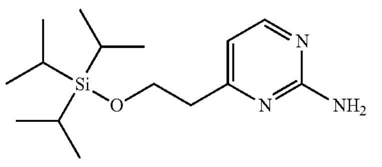 [SMILES: CC(C)[Si](OCCc1ccnc(N)n1)(C(C)C)C(C)C]

[Procedure A, Condition 1] [3-benzoylpyridine]

White solid (38 mg, 51% yield); m.p.: 96-98° C.; $^{1}H$ NMR (600 MHz, $CD_2Cl_2$) δ 8.12 (d, J=5.0 Hz, 1H), 6.56 (d, J=5.0 Hz, 1H), 5.18 (br s, 2H), 4.01 (t, J=6.4 Hz, 2H), 2.76 (t, J=6.4 Hz, 2H), 1.11-0.96 (m, 21H); $^{13}C\{^{1}H\}$ NMR (150 MHz, $CD_2Cl_2$) δ 169.9, 163.6, 158.0, 112.1, 62.6, 41.7, 18.1, 12.4; $^{29}Si$ NMR (80 MHz, $CD_2Cl_2$) δ 13.0; IR ($cm^{-1}$): 3326, 3164, 2940, 2889, 2864, 2742, 1659, 1567, 1459, 1342, 1223, 1090, 1013, 880, 830; HRMS (EI): Calculated for $C_{15}H_{29}N_3OSi$ $[M]^+$: 295.2080; Found: 295.2083.

After separation with chromatography, 97 mg of 3-benzoylpyridine (recovery yield: 96%) was obtained.

[Example 20] Preparation of N-methyl-N-(4-phenylpyrimidin-2-yl)acetamide (20)

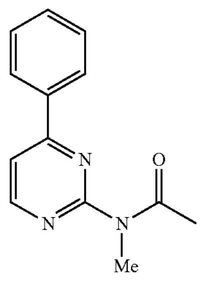 [SMILES: CC(=O)N(C)c1nccc(-c2ccccc2)n1]

[Procedure B, Condition 1] [N-methylacetamide]

White solid (49 mg, 86% yield); m.p.: 107-109° C.; $^{1}H$ NMR (500 MHz, $CD_2Cl_2$) δ 8.67 (d, J=5.2 Hz, 1H), 8.14-8.09 (m, 2H), 7.56-7.50 (m, 3H), 7.48 (d, J=5.2 Hz, 1H), 3.52 (s, 3H), 2.51 (s, 3H); $^{13}C\{^{1}H\}$ NMR (125 MHz, $CD_2Cl_2$) δ 172.6, 165.0, 162.1, 158.8, 136.7, 131.6, 129.4, 127.5, 112.3, 33.6, 26.0; IR ($cm^{-1}$): 3077, 2928, 1677, 1572, 1543, 1448, 1365, 1325, 1294, 1168, 979, 859; HRMS (EI): Calculated for $C_{13}H_{13}N_3O$ $[M]^+$: 227.1059; Found: 227.1054.

[Example 21] Preparation of N-methyl-N-(pyrimidin-2-yl)acetamide (21)

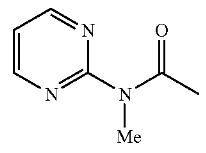

[Procedure B, Condition 1] [N-methylacetamide]

Slightly yellow solid (24 mg, 65% yield); m.p.: 49-51° C.; $^{1}H$ NMR (500 MHz, $CD_2Cl_2$) δ 8.62 (d, J=4.8 Hz, 2H), 7.04 (dd, J=4.8, 4.8 Hz, 1H), 3.42 (s, 3H), 2.39 (s, 3H); $^{13}C\{^{1}H\}$ NMR (125 MHz, $CD_2Cl_2$) δ 172.4, 161.9, 158.1, 118.9, 33.6, 25.7; IR ($cm^{-1}$): 3133, 3087, 3046, 2994, 2942, 2856, 1664, 1561, 1434, 1394, 1320, 1259, 1158, 981, 937, 813; HRMS (ESI): Calculated for $C_7H_{10}N_3O$ $[M+H]^+$: 152.0818; Found: 152.0805.

[Example 22] Preparation of N-methyl-N-(4-methylpyrimidin-2-yl)acetamide (22)

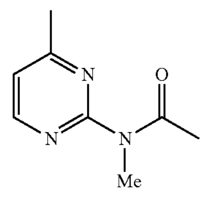

[Procedure B, Condition 1] [N-methylacetamide]

Yellow solid (30 mg, 72% yield); m.p.: 61-63° C.; $^{1}H$ NMR (500 MHz, $CD_2Cl_2$) δ 8.46 (d, J=4.9 Hz, 1H), 6.91 (d, J=4.9 Hz, 1H), 3.41 (s, 3H), 2.48 (s, 3H), 2.38 (3H); $^{13}C\{^{1}H\}$NMR (125 MHz, $CD_2Cl_2$) δ 172.5, 168.7, 161.8, 157.6, 116.5, 33.6, 25.6, 24.2; IR ($cm^{-1}$): 3078, 3005, 2958, 2918, 2850, 1672, 1582, 1555, 1437, 1361, 1322, 1256, 1200, 1168, 1021, 982, 838; HRMS (ESI): Calculated for $C_8H_{12}N_3O$ $[M+H]^+$: 166.0975; Found: 166.0976.

[Example 23] Preparation of N-(4-methoxypyrimidin-2-yl)-N-phenylacetamide (23)

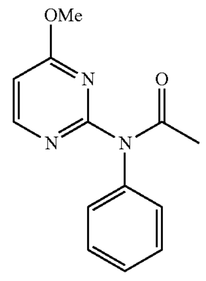 [SMILES: COc1ccnc(N(C(C)=O)c2ccccc2)n1]

[Procedure B, Condition 1] [acetanilide]

Creamy solid (40 mg, 66% yield); $^{1}H$ NMR (500 MHz, $CD_2Cl_2$) 8.29 (d, J=5.7 Hz, 1H), 7.45-7.39 (m, 2H), 7.36-7.31 (m, 1H), 7.25-7.19 (m, 2H), 6.52 (d, J=5.7 Hz, 1H), 3.87 (s, 3H), 2.45 (s, 3H); $^{13}C\{^{1}H\}$ NMR (125 MHz, $CD_2Cl_2$) δ 172.1, 170.6, 161.3, 158.4, 142.0, 129.4, 129.0, 127.7, 104.8, 54.3, 25.7; HRMS (ESI) Calculated for $C_{13}H_{14}N_3O_2[M+H]^+$: 244.1081; Found: 244.1073.

[Example 24] Preparation of N-(4,6-dimethylpyrimidin-2-yl)-N-methylacetamide (24)

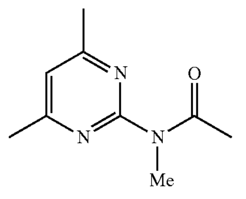

[Procedure B, Condition 1] [N-methylacetamide]

Slightly yellow solid (33 mg, 73% yield); m.p.: 68-70° C.; $^{1}H$ NMR (500 MHz, $CD_2Cl_2$) δ 6.79 (s, 1H), 3.38 (s, 3H), 2.42 (s, 6H), 2.35 (s, 3H); $^{13}C\{^{1}H\}$ NMR (125 MHz, $CD_2Cl_2$) δ 172.5, 168.1, 161.6, 115.9, 33.6, 25.5, 24.0; IR ($cm^{-1}$): 3075, 2999, 2958, 2922, 2852, 1665, 1590, 1422, 1365, 1321, 1199, 1028, 865; HRMS (EI): Calculated for $C_9H_{13}N_3O$ $[M]^+$: 179.1059; Found: 179.1060.

[Example 25] Preparation of N-methyl-N-[4-(pyridin-3-yl)pyrimidin-2-yl]acetamide (25)

In step 1, trifluoromethanesulfonic acid (22 μL, 37 mg, 0.25 mmol, 1.0 equiv.) was added to the reaction mixture to selectively oxidize a pyrimidine ring.

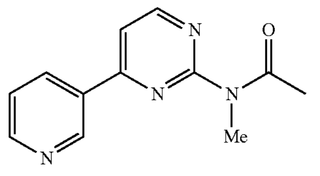 [SMILES: CC(=O)N(C)c1nccc(-c2cccnc2)n1]

[Procedure B, Condition 1] [N-methylacetamide]

Slightly yellow solid (18 mg, 32% yield); m.p.: 143-145° C.; $^{1}H$ NMR (600 MHz, $CD_2Cl_2$) δ 9.29 (s, 1H), 8.73 (d, J=4.7 Hz, 1H), 8.72 (d, J=5.2 Hz, 1H), 8.39 (d, J=7.9 Hz, 1H), 7.50 (d, J=5.2 Hz, 1H), 7.46 (dd, J=4.7, 7.9 Hz, 1H), 3.53 (s, 3H), 2.52 (s, 3H); $^{13}C\{^{1}H\}$ NMR (125 MHz, $CD_2Cl_2$) δ 172.7, 162.9, 162.2, 159.2, 152.3, 149.0, 134.8, 132.4, 124.1, 112.3, 33.6, 26.2; IR ($cm^{-1}$): 3076, 2960, 2921, 2851, 1676, 1572, 1544, 1433, 1366, 1340, 1296, 1259, 1167, 1022, 980, 861; HRMS (EI): Calculated for $C_{12}H_{12}N_4O$ $[M]^+$: 228.1011; Found: 228.1012.

[Example 26] Preparation of N-[5-(4-chlorophenyl)-4-ethylpyrimidin-2-yl]-N-methylacetamide (26)

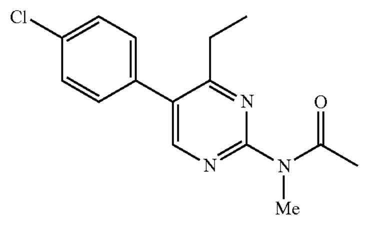 [SMILES: CCc1nc(N(C)C(C)=O)ncc1-c1ccc(Cl)cc1]

[Procedure B, Condition 1] [N-methylacetamide]

White solid (35 mg, 49% yield); m.p.: 64-66° C.; $^{1}H$ NMR (500 MHz, $CD_2Cl_2$) δ 8.39 (s, 1H), 7.49-7.45 (m, 2H), 7.30-7.27 (m, 2H), 3.48 (s, 3H), 2.73 (q, J=7.5 Hz, 2H), 2.47 (s, 3H), 1.22 (t, J=7.5 Hz, 3H); $^{13}C\{^{1}H\}$ NMR (125 MHz, $CD_2Cl_2$) δ 172.6, 170.0, 160.9, 157.6, 134.8, 134.5, 131.0, 129.3, 128.8, 33.6, 28.6, 26.0, 12.6; IR ($cm^{-1}$): 2969, 2934, 2872, 1901, 1665, 1579, 1540, 1441, 1368, 1310, 1259, 1159, 1086, 1019, 974, 828, 721, 648; HRMS (EI): Calculated for $C_{15}H_{16}ClN_3O$ $[M]^+$: 289.0982; Found: 289.0979.

[Example 27] Preparation of (E)-N-[4-(4-chlorostyryl)pyrimidin-2-yl]-N-methylacetamide (27)

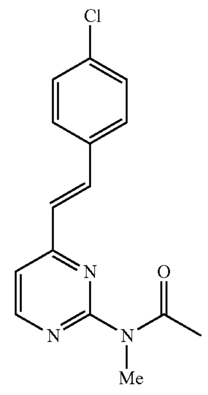 [SMILES: CC(=O)N(C)c1nccc(/C=C/c2ccc(Cl)cc2)n1]

[Procedure B, Condition 1] [N-methylacetamide]

White solid (31 mg, 43% yield); m.p.: 108-110° C.; $^{1}H$ NMR (500 MHz, $CD_2Cl_2$) δ 8.58 (d, J=5.1 Hz, 1H), 7.84 (d, J=15.9 Hz, 1H), 7.59-7.55 (m, 2H), 7.42-7.38 (m, 2H), 7.07-7.02 (m, 2H), 3.48 (s, 3H), 2.46 (s, 3H); $^{13}C\{^{1}H\}$ NMR (125 MHz, $CD_2Cl_2$) δ 172.6, 163.2, 161.9, 159.8, 136.3, 135.5, 134.6, 129.5, 129.3, 126.5, 114.7, 33.7, 25.9; IR ($cm^{-1}$): 3059, 2923, 1668, 1571, 1541, 1454, 1382, 1329, 1165, 1085, 966, 830, 689, 638, 602; HRMS (EI): Calculated for $C_{15}H_{14}ClN_3O$ $[M]^+$: 287.0825; Found: 287.0827.

[Example 28] Preparation of N-[4-(benzofuran-2-yl)pyrimidin-2-yl]-N-methylacetamide (28)

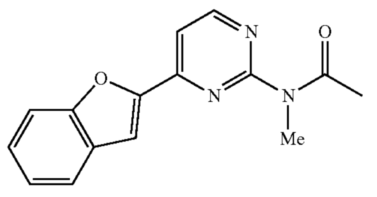 [SMILES: CC(=O)N(C)c1nccc(-c2cc3ccccc3o2)n1]

[Procedure B, Condition 1] [N-methylacetamide]

White solid (54 mg, 81% yield); m.p.: 117-119° C.; $^1H$ NMR (600 MHz, $CD_2Cl_2$) δ 8.71 (d, J=4.9 Hz, 1H), 7.73-7.69 (m, 1H), 7.63 (s, 1H), 7.61-7.57 (m, 1H), 7.53 (d, J=4.9 Hz, 1H), 7.46-7.40 (m, 1H), 7.35-7.29 (m, 1H), 3.51 (s, 3H), 2.53 (s, 3H); $^{13}C\{^1H\}$ NMR (150 MHz, $CD_2Cl_2$) δ 172.6, 161.9, 159.3, 156.5, 156.2, 153.4, 128.6, 127.1, 124.1, 122.8, 112.1, 111.2, 109.0, 33.6, 26.1; IR ($cm^{-1}$): 3114, 3067, 2937, 2855, 1673, 1602, 1569, 1534, 1431, 1384, 1326, 1203, 1179, 1124, 983, 842, 809; HRMS (EI): Calculated for $C_{15}H_{13}N_3O_2$ $[M]^+$: 267.1008; Found: 267.1010.

[Example 29] Preparation of N-[2-(N-methylacetamido)pyrimidin-4-yl]benzamide (29)

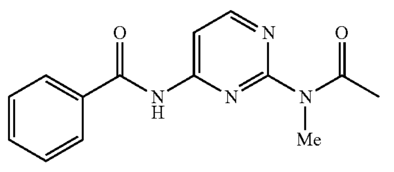 [SMILES: CC(=O)N(C)c1nccc(NC(=O)c2ccccc2)n1]

[Procedure B, Condition 1] [N-methylacetamide]

White solid (57 mg, 84% yield); m.p.: 144-146° C.; $^1H$ NMR (500 MHz, $CD_2Cl_2$) δ 8.74 (br s, 1H), 8.57 (d, J=5.6 Hz, 1H), 8.03 (d, J=5.6 Hz, 1H), 7.97-7.92 (m, 2H), 7.66-7.61 (m, 1H), 7.58-7.51 (m, 2H), 3.41 (s, 3H), 2.41 (s, 3H); $^{13}C\{^1H\}$NMR (125 MHz, $CD_2Cl_2$) δ 172.5, 166.5, 161.4, 159.7, 158.5, 133.7, 133.3, 129.3, 127.8, 105.9, 33.7, 25.8; IR ($cm^{-1}$): 3563, 3213, 3154, 3062, 2924, 2851, 1683, 1573, 1510, 1391, 1296, 1258, 1105, 990, 890, 843; HRMS (EI): Calculated for $C_{14}H_{14}N_4O_2$ $[M]^+$: 270.1117; Found: 270.1115.

[Example 30] Preparation of dabrafenib (30)

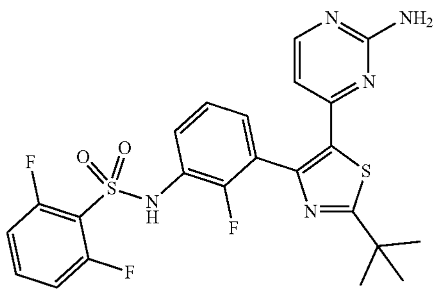 [SMILES: CC(C)(C)c1nc(-c2cccc(NS(=O)(=O)c3c(F)cccc3F)c2F)c(-c2ccnc(N)n2)s1]

[Procedure A, Condition 1] [3-(trifluoromethyl)pyridine]

Light brown solid (77 mg, 59% yield); m.p.: 217-219° C.; $^1H$ NMR (500 MHz, $CD_2Cl_2$) δ 7.88 (d, J=5.3 Hz, 1H), 7.70-7.64 (m, 1H), 7.53-7.46 (m, 1H), 7.39-7.34 (m, 1H), 7.23 (dd, J=7.9 Hz, 1H), 7.01-6.95 (m, 2H), 6.16 (d, J=5.3 Hz, 1H), 5.28 (br s, 2H), 1.44 (s, 9H); $^{13}C\{^1H\}$ NMR (125 MHz, $CD_2Cl_2$) δ 183.2, 163.2, 160.1 (dd, J=258.9, 3.5 Hz), 159.6, 158.5, 152.0 (d, J=248.6 Hz), 146.0, 135.8 (t, J=11.2 Hz), 134.3, 129.0 (d, J=2.3 Hz), 125.3 (d, J=4.5 Hz), 124.8 (4), 124.8(1) (d, J=12.2 Hz), 124.7(9) (d, J=11.5 Hz), 117.4 (t, J=15.7 Hz), 113.5 (dd, J=22.9, 3.6 Hz), 107.6, 38.4, 30.8; 19F NMR (376 MHz, $CD_2Cl_2$) δ −107.6 (d, J=4.0 Hz), −129.1 (t, J=4.0 Hz); IR ($cm^{-1}$): 3530, 3417, 3081, 2962, 2871, 1607, 1572, 1460, 1352, 1275, 1235, 1173, 999.

[Example 31] Preparation of Encorafenib Analog (31)

In step 1, $MeReO_3$ (20 mol %) and aq. $H_2O_2$ (4.0 equiv.) were used.

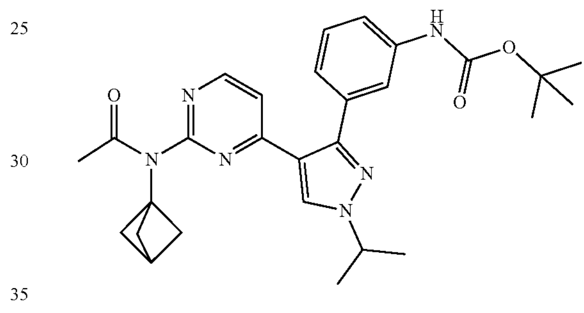

[Procedure B, Condition 1] [N-(bicyclo[1.1.1]pentan-1-yl)acetamide]

White solid (29 mg, 23% yield, 32% brsm); m.p.: 83-85° C.; $^1H$ NMR (600 MHz, $CD_2Cl_2$) δ 8.43 (d, J=4.9 Hz, 1H), 8.13 (s, 1H), 7.55 (s, 1H), 7.49-7.42 (m, 1H), 7.38-7.31 (m, 1H), 7.22-7.15 (m, 1H), 7.02 (d, J=4.9 Hz, 1H), 6.76 (br s, 1H), 4.56 (sep, 6.5 Hz, 1H), 2.44 (s, 1H), 2.16 (s, 6H), 1.99 (s, 3H), 1.58 (d, J=6.5 Hz, 6H) (overlap with the signal of residual water), 1.49 (s, 9H); $^{13}C\{^1H\}$ NMR (150 MHz, $CD_2Cl_2$) δ 171.4, 161.8, 160.7, 158.6, 153.0, 150.4, 139.4, 134.9, 129.9, 129.5, 123.9, 119.4, 118.7, 117.9, 115.5, 80.8, 55.0, 53.7, 30.1, 28.4, 25.1, 24.4, 23.0; IR ($cm^{-1}$): 3275, 2976, 2917, 2879, 1722, 1661, 1576, 1554, 1514, 1366, 1335, 1235, 1156, 1066, 1050, 853; HRMS (FAB): Calculated for $C_{28}H_{35}N_6O_3$ $[M+H]^+$: 503.2765; Found: 503.2774.

After separation with chromatography, 26 mg of S8 (recovery yield: 28%) was obtained.

[Example 32] Preparation of Ruxolitinib Derivative (32)

After N-oxidation of S9 (428 mg, 0.928 mmol) under standard conditions, the reaction mixture was concentrated in vacuum. A residue was purified with silica gel chromatography while eluting with a solvent mixture of dichloromethane/methanol (100/0 to 90/10 (v/v)) to obtain 131 mg of unidentified N-oxide (0.275 mmol, yield: 30%) as a yellow solid, and obtain 124 mg of S11 (29% of recovery yield). The obtained N-oxide was directly applied to Procedure B.

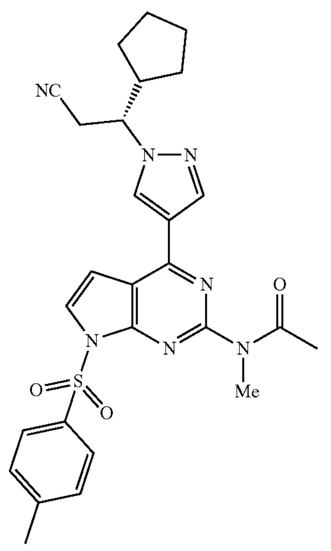 [SMILES: CC(=O)N(C)c1nc(-c2cnn([C@H](CC#N)C3CCCC3)c2)c2ccn(S(=O)(=O)c3ccc(C)cc3)c2n1]

[Procedure B, Condition 1] [N-methylacetamide]

White solid (99 mg, 68% yield from N-oxide); m.p.: 93-95° C.; $^{1}H$ NMR (500 MHz, $CD_2Cl_2$) δ 8.26 (s, 1H), 8.24 (s, 1H), 8.03-7.98 (m, 2H), 7.73 (d, J=4.1 Hz, 1H), 7.36-7.31 (m, 2H), 6.86 (d, J=4.1 Hz, 1H), 4.26 (ddd, J=3.7, 9.6, 9.6 Hz, 1H), 3.50 (s, 3H), 3.13 (dd, J=9.1, 17.1 Hz, 1H), 2.95 (dd, J=3.7, 17.1 Hz, 1H), 2.60-2.49 (m, 1H), 2.46 (s, 3H), 2.39 (s, 3H), 1.98-1.89 (m, 1H), 1.77-1.43 (m, 5H), 1.33-1.24 (m, 1H), 1.24-1.14 (m, 1H); $^{13}C\{^{1}H\}$ NMR (125 MHz, $CD_2Cl_2$) δ 172.5, 157.4, 153.0, 152.5, 146.6, 140.4, 135.1, 130.9, 130.2, 128.5, 126.4, 120.9, 117.2, 112.4, 104.0, 64.8, 44.8, 34.0, 30.4, 30.3, 25.8, 25.7, 25.1, 23.8, 21.8; IR ($cm^{-1}$): 3136, 3116, 2946, 2868, 2248, 1664, 1571, 1511, 1443, 1367, 1174, 1143, 1088, 1006, 976, 806; HRMS (EI): Calculated for $C_{27}H_{29}N_7O_3S$ $[M]^+$: 531.2053; Found: 531.2056.

The above description of the present invention is for illustration, and those with ordinary knowledge in the art will appreciate that various modifications and alterations may be easily made without departing from the spirit or essential feature of the present invention. Therefore, it should be understood that the exemplary embodiments described above are not restrictive, but illustrative in all aspects.

The invention claimed is:

1. A method of preparing a pyrimidin-2-amine compound, the method comprising:

1) Oxidizing a pyrimidine compound of the following Chemical Formula 2 to prepare a pyrimidine-N-oxide intermediate;

2) Following step 1), in-situ activating the pyrimidine-N-oxide intermediate in the presence of a trifluoromethanesulfonic anhydride and reacting with a pyridine reagent of the following Chemical Formula 3-1 to prepare a pyrimidine-2-pyridinium salt; and 3) Following step 2), aminolyzing the pyrimidine-2-pyridinium salt to prepare a pyrimidin-2-amine compound of the following Chemical Formula 1-1, wherein steps 1) and 2) are performed as in-situ continuous processes without a separation process:

[Chemical Formula 1-1]

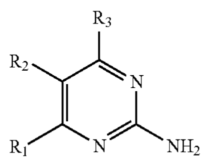

[Chemical Formula 2]

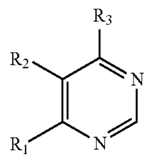

[Chemical Formula 3-1]

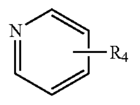

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O) Ar, or $R_1$ to $R_3$ may be linked to an adjacent substituent to form a ring;

$R_4$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, $—OSiR_{a1}R_{a2}R_{a3}$, $-L_1-NR_{b1}-L_2-R_{b2}$, and $—CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is $-L_3-R_{d1}$, $L_3$ is C1-C20 alkylene, and $R_{d1}$ is cyano, halogen, or nitro.

2. The method of preparing a pyrimidin-2-amine compound of claim 1, wherein the oxidation in step 1) is performed under an oxidizing agent, a rhenium catalyst, or a combination thereof.

3. The method of preparing a pyrimidin-2-amine compound of claim 2, wherein the rhenium catalyst is one or a mixture of two or more selected from methyltrioxorhenium (MTO), ethyltrioxorhenium (ETO), rhenium (VII) oxide ($Re_2O_7$), rhenium (V) oxide ($Re_2O_5$), rhenium (IV) oxide ($ReO_2$), and ammonium perrhenate (APR), and the oxidizing agent is hydrogen peroxide or a hydrogen peroxide adduct.

4. The method of preparing a pyrimidin-2-amine compound of claim 2, wherein the rhenium catalyst is used at 1.0 to 30.0 mol % with respect to the pyrimidine compound of Chemical Formula 2.

5. The method of preparing a pyrimidin-2-amine compound of claim 2, wherein the oxidizing agent is used at 1 to 5 equivalents with respect to the pyrimidine compound of Chemical Formula 2.

6. The method of preparing a pyrimidin-2-amine compound of claim 1, wherein the trifluoromethanesulfonic anhydride in step 2) is used at 1 to 3 equivalents with respect to the pyrimidine compound of Chemical Formula 2.

7. The method of preparing a pyrimidin-2-amine compound of claim 1, wherein the pyridine reagent of Chemical Formula 3-1 in step 2) is used at 2 to 3 equivalents with respect to the pyrimidine compound of Chemical Formula 2.

8. The method of preparing a pyrimidin-2-amine compound of claim 1, wherein the aminolysis in step 3) is performed in the presence of ammonia water.

9. A method of preparing a cyclic (2-enamino)pyrimidine compound, the method comprising:

1) Oxidizing a pyrimidine compound of the following Chemical Formula 2 to prepare a pyrimidine-N-oxide intermediate;
2) Following step 1), in-situ activating the pyrimidine-N-oxide intermediate in the presence of a trifluoromethanesulfonic anhydride and reacting with a pyridine reagent of the following Chemical Formula 3-2 to prepare a pyrimidine-2-pyridinium salt; and
3) Following step 2), partially reducing the pyrimidine-2-pyridinium salt to prepare a cyclic (2-enamino)pyrimidine compound of the following Chemical Formula 1-2, wherein steps 1) and 2) are performed as in-situ continuous processes without a separation process:

[Chemical Formula 1-2]

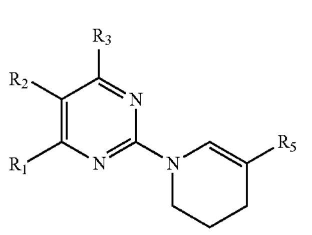

[Chemical Formula 2]

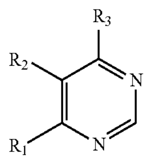

[Chemical Formula 3-2]

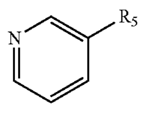

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(±O)$Ar_1$, or $R_1$ to $R_3$ may be linked to an adjacent substituent to form a ring;

$R_5$ is halo C1-C20 alkyl, cyano, C1-C20 alkylcarbonyl, or C6-C20 arylcarbonyl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, $—OSiR_{a1}R_{a2}R_{a3}$, $-L_1-NR_{b1}-L_2-R_{b2}$, and $-CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is $-L_3-R_{d1}$, $L_3$ is C1-C20 alkylene, and Rai is cyano, halogen, or nitro.

10. The method of preparing a cyclic (2-enamino)pyrimidine compound of claim 9, wherein the pyridine reagent of Chemical Formula 3-2 in step 2) is used at 2 to 3 equivalents with respect to the pyrimidine compound of Chemical Formula 2.

11. The method of preparing a cyclic (2-enamino)pyrimidine compound of claim 9, wherein the partial reduction in step 3) is performed in the presence of hydrogen gas and $PtO_2$.

12. The method of preparing a cyclic (2-enamino)pyrimidine compound of claim 11, wherein $PtO_2$ is used at 1.0 to 20.0 mol % with respect to the pyrimidine compound of Chemical Formula 2.

13. A method of preparing a pyrimidin-2-substituted amine compound, the method comprising:

1) Oxidizing a pyrimidine compound of the following Chemical Formula 2 to prepare a pyrimidine-N-oxide intermediate;
2) Following step 1), reacting the pyrimidine-N-oxide intermediate with an imidoyl chloride compound of the following Chemical Formula 4-1 in the presence of a trifluoromethanesulfonic anhydride to prepare a pyrimidin-2-iminium salt; and
3) Following step 2), treating the pyrimidin-2-iminium salt with sodium bicarbonate, or reducing or hydrolyzing the pyrimidin-2-iminium salt to prepare a pyrimidin-2-substituted amine compound of the following Chemical Formula 1-3, wherein steps 1) and 2) are performed as in-situ continuous processes without a separation process:

[Chemical Formula 1-3]

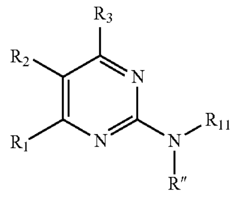

[Chemical Formula 2]

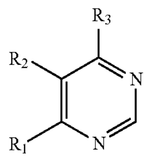

[Chemical Formula 4-1]

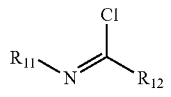

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O) $Ar_1$, or $R_1$ to $R_3$ may be linked to an adjacent substituent to form a ring;

R" is hydrogen, —C(═O) $R_{12}$, or $—CH_2R_{12}$;

$R_{11}$ is C1-C20 alkyl, C6-C20 aryl, allyl, haloC1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl;

$R_{12}$ is C1-C20 alkyl or C6-C20 aryl;

R' is hydrogen or C1-C20 alkyl;

$Ar_1$ is C6-C20 aryl or C3-C20 heteroaryl;

the alkyl, cycloalkyl, aryl, alkoxy, alkenyl, and heteroaryl of $R_1$ to $R_3$ may be further substituted by any one or more selected from C1-C20 alkyl, halogen, C1-C20 alkoxy, hydroxy, C6-C20 aryl, halo C6-C20 aryl, —$OSiR_{a1}R_{a2}R_{a3}$, -$L_1$-$NR_{b1}$-$L_2$-$R_{b2}$, and —$CHR_{c1}R_{c2}$;

$R_{a1}$, $R_{a2}$, and $R_{a3}$ are independently of one another C1-C20 alkyl, C3-C20 cycloalkyl, or C6-C20 aryl;

$L_1$ is C6-C20 arylene or halo C6-C20 arylene, and $L_2$ is $SO_2$ or C═O;

$R_{b1}$ is hydrogen or C1-C20 alkyl;

$R_{b2}$ is C1-C20 alkoxy, C6-C20 aryl, or halo C6-C20 aryl;

$R_{c1}$ is C3-C20 cycloalkyl; and $R_{c2}$ is -$L_3$-$R_{d1}$, $L_3$ is C1-C20 alkylene, and Rai is cyano, halogen, or nitro.

14. The method of preparing a pyrimidin-2-substituted amine compound of claim 13, wherein the imidoyl chloride compound of Chemical Formula 4-1 is prepared by reacting an amide compound of the following Chemical Formula 4 with oxalyl chloride in the presence of an organic base:

[Chemical Formula 4]

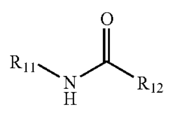

wherein $R_{11}$ is C1-C20 alkyl, C6-C20 aryl, allyl, haloC1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl; and $R_{12}$ is C1-C20 alkyl or C6-C20 aryl.

15. The method of preparing a pyrimidin-2-substituted amine compound of claim 13, wherein the trifluoromethanesulfonic anhydride in step 2) is used at 1.0 to 3.0 equivalents with respect to the pyrimidine compound of Chemical Formula 2.

16. The method of preparing a pyrimidin-2-substituted amine compound of claim 13, wherein the imidoyl chloride compound of Chemical Formula 4-1 in step 2) is used at 2.0 to 3.0 equivalents with respect to the pyrimidine compound of Chemical Formula 2.

17. The method of preparing a pyrimidin-2-substituted amine compound of claim 13, wherein step 3) is preparing a pyrimidin-2-amide compound of the following Chemical Formula 1-3A by a treatment with sodium bicarbonate:

[Chemical Formula 1-3A]

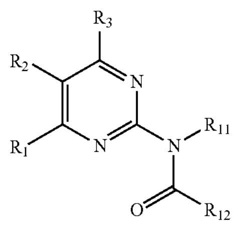

wherein $R_1$, $R_2$, and $R_3$ are independently of one another hydrogen, C1-C20 alkyl, C3—C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

$R_{11}$ is C1-C20 alkyl, C6-C20 aryl, allyl, haloC1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl; and $R_{12}$ is C1-C20 alkyl or C6-C20 aryl.

18. The method of preparing a pyrimidin-2-substituted amine compound of claim 13, wherein step 3) is treating with a reducing agent selected from sodium triacetoxyborohydride ($Na(CH_3COO)_3BH$), sodium borohydride ($NaBH_4$), sodium cyanoborohydride ($NaBH_3CN$), zinc borohydride ($Zn(BH_4)_2$), lithium aluminum hydride ($LiAlH_4$), and lithium cyanoborohydride ($LiBH_3CN$) to prepare a pyrimidin-2-disubstituted amine compound of the following Chemical Formula 1-3B:

[Chemical Formula 1-3B]

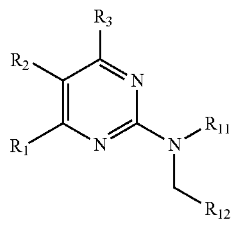

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring;

$R_{11}$ is C1-C20 alkyl, C6-C20 aryl, allyl, haloC1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl; and $R_{12}$ is C1-C20 alkyl or C6-C20 aryl.

19. The method of preparing a pyrimidin-2-substituted amine compound of claim 13, wherein step 3) is treating with methanol and sodium hydroxide to prepare a pyrimidin-2-monosubstituted amine compound of the following Chemical Formula 1-3C:

[Chemical Formula 1-3C]

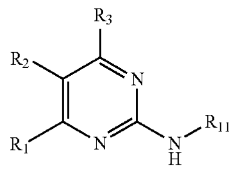

wherein $R_1$, $R_2$, and $R_3$ are independently of one another hydrogen, C1-C20 alkyl, C3-C20 cycloalkyl, C6-C20 aryl, C1-C20 alkoxy, C2-C20 alkenyl, C3-C20 heteroaryl, or —NR'C(═O)$Ar_1$, or $R_1$ to $R_3$ may be linked to an adjacent substituent to form a ring; and $R_{11}$ is C1-C20 alkyl, C6-C20 aryl, allyl, haloC1-C20 alkyl, C6-C20 aryl C1-C20 alkyl, or C3-C20 cycloalkyl, and the cycloalkyl may be further substituted by one or more selected from halogen, halo C1-C20 alkyl, and halo C6-C20 aryl.

* * * * *